(12) United States Patent
Spenser et al.

(10) Patent No.: US 7,276,078 B2
(45) Date of Patent: Oct. 2, 2007

(54) PARAVALVULAR LEAK DETECTION, SEALING, AND PREVENTION

(75) Inventors: Benjamin Spenser, Caesarea (IL); Netanel Benichou, Hof-Carmel (IL); Assaf Bash, Givat Ada (IL)

(73) Assignee: Edwards Lifesciences PVT, Irvine, CA (US)

( * ) Notice: Subject to any disclaimer, the term of this patent is extended or adjusted under 35 U.S.C. 154(b) by 434 days.

(21) Appl. No.: 10/883,575

(22) Filed: Jun. 30, 2004

(65) Prior Publication Data

US 2006/0004442 A1 Jan. 5, 2006

(51) Int. Cl.
*A61F 2/24* (2006.01)

(52) U.S. Cl. .................................... 623/1.24
(58) Field of Classification Search ......... 623/2.1–2.41
See application file for complete search history.

(56) References Cited

U.S. PATENT DOCUMENTS

| | | | |
|---|---|---|---|
| 3,409,013 A | 11/1968 | Berry | |
| 3,587,115 A | 6/1971 | Shiley | |
| 3,671,979 A | 6/1972 | Moulopoulos | |
| 3,714,971 A | 2/1973 | Edwards et al. | |
| 3,755,823 A * | 9/1973 | Hancock | 623/2.18 |
| 4,035,849 A | 7/1977 | Angell et al. | |
| 4,056,854 A | 11/1977 | Boretos et al. | |
| 4,106,129 A | 8/1978 | Carpentier et al. | |
| 4,222,126 A | 9/1980 | Boretos et al. | |
| 4,297,749 A | 11/1981 | Davis et al. | |
| 4,339,831 A | 7/1982 | Johnson | |
| 4,343,048 A | 8/1982 | Ross et al. | |
| 4,345,340 A | 8/1982 | Rosen | |
| 4,470,157 A | 9/1984 | Love | |
| 4,574,803 A | 3/1986 | Storz | |
| 4,592,340 A | 6/1986 | Boyles | |
| 4,612,011 A | 9/1986 | Kautzky | |
| 4,655,771 A | 4/1987 | Wallsten | |
| 4,733,665 A | 3/1988 | Palmaz | |
| 4,777,951 A | 10/1988 | Cribier et al. | |
| 4,787,899 A | 11/1988 | Lazarus | |
| 4,787,901 A | 11/1988 | Baykut | |
| 4,796,629 A | 1/1989 | Grayzel | |

(Continued)

FOREIGN PATENT DOCUMENTS

DE 195 32 846 3/1997

(Continued)

OTHER PUBLICATIONS

Transcatheter Umbrella Closure of Valvular and Paravalvular Leaks, Hourihan et al., Journal of the American College of Cardiology, vol. 20, No. 6, pp. 1371-1377, (1992).

*Primary Examiner*—Suzette Gherbi
(74) *Attorney, Agent, or Firm*—David L. Hauser

(57) ABSTRACT

The present invention provides a series of new percutaneous concepts of paravalvular repairs including identifying the leak location, several repair techniques and finally built-in means for leak prevention, built on percutaneous valves. A catheter-delivered device locates cavities occurring between a prosthetic valve and the wall of the body vessel where the valve is implanted, the cavities producing paravalvular leaks during diastole, the device comprising at least one of a plurality of flexible wires, the wire having attached to it a balloon, wherein the balloon is pulled by the leak through the cavity and wherein the wire then serves to mark the cavity location.

6 Claims, 20 Drawing Sheets

U.S. PATENT DOCUMENTS

| | | | |
|---|---|---|---|
| 4,878,495 A | 11/1989 | Grayzel | |
| 4,878,906 A | 11/1989 | Lindemann et al. | |
| 4,883,458 A | 11/1989 | Shiber | |
| 4,966,604 A | 10/1990 | Reiss | |
| 4,979,939 A | 12/1990 | Shiber | |
| 4,986,830 A | 1/1991 | Owens et al. | |
| 4,994,077 A | 2/1991 | Dobben | |
| 5,007,896 A | 4/1991 | Shiber | |
| 5,026,366 A | 6/1991 | Leckrone | |
| 5,047,041 A | 9/1991 | Samuels | |
| 5,059,177 A | 10/1991 | Towne et al. | |
| 5,085,635 A | 2/1992 | Cragg | |
| 5,089,015 A | 2/1992 | Ross | |
| 5,152,771 A | 10/1992 | Sabbaghian et al. | |
| 5,163,953 A | 11/1992 | Vince | |
| 5,167,628 A | 12/1992 | Boyles | |
| 5,295,958 A | 3/1994 | Shturman | |
| 5,332,402 A | 7/1994 | Teitelbaum | |
| 5,370,685 A * | 12/1994 | Stevens | 623/2.11 |
| 5,397,351 A | 3/1995 | Pavcnik et al. | |
| 5,411,552 A | 5/1995 | Andersen et al. | |
| 5,443,446 A | 8/1995 | Shturman | |
| 5,480,424 A | 1/1996 | Cox | |
| 5,545,209 A | 8/1996 | Roberts et al. | |
| 5,554,185 A | 9/1996 | Block et al. | |
| 5,591,195 A | 1/1997 | Taheri et al. | |
| 5,716,417 A | 2/1998 | Girard et al. | |
| 5,749,890 A | 5/1998 | Shaknovich | |
| 5,855,597 A | 1/1999 | Jayaraman | |
| 5,925,063 A | 7/1999 | Khosravi | |
| 5,957,949 A | 9/1999 | Leonhardt et al. | |
| 6,027,525 A | 2/2000 | Suh et al. | |
| 6,132,473 A | 10/2000 | Williams et al. | |
| 6,168,614 B1 | 1/2001 | Andersen et al. | |
| 6,171,335 B1 | 1/2001 | Wheatley et al. | |
| 6,221,091 B1 | 4/2001 | Khosravi | |
| 6,245,102 B1 | 6/2001 | Jayaraman | |
| 6,299,637 B1 | 10/2001 | Shaolia et al. | |
| 6,302,906 B1 | 10/2001 | Goicoechea et al. | |
| 6,425,916 B1 | 7/2002 | Garrison et al. | |
| 6,440,164 B1 | 8/2002 | Di Matteo et al. | |
| 6,454,799 B1 | 9/2002 | Schreck | |
| 6,458,153 B1 | 10/2002 | Bailey et al. | |
| 6,461,382 B1 | 10/2002 | Cao | |
| 6,468,660 B2 | 10/2002 | Ogle et al. | |
| 6,482,228 B1 * | 11/2002 | Norred | 623/2.17 |
| 6,488,704 B1 | 12/2002 | Connelly et al. | |
| 6,569,196 B1 | 5/2003 | Vesely | |
| 6,605,112 B1 | 8/2003 | Moll et al. | |
| 6,730,118 B2 | 5/2004 | Spenser et al. | |
| 6,769,434 B2 | 8/2004 | Liddicoat | |
| 6,786,925 B1 | 9/2004 | Schoon | |
| 6,790,229 B1 | 9/2004 | Berreklouw | |
| 6,797,002 B2 | 9/2004 | Spence | |
| 6,821,297 B2 | 11/2004 | Snyders | |
| 6,830,584 B1 | 12/2004 | Seguin | |
| 6,830,585 B1 | 12/2004 | Artof | |
| 6,866,650 B2 | 3/2005 | Stevens | |
| 6,872,223 B2 | 3/2005 | Roberts | |
| 6,875,231 B2 | 4/2005 | Anduiza | |
| 6,893,460 B2 | 5/2005 | Spenser et al. | |
| 6,908,481 B2 | 6/2005 | Cribier | |
| 6,951,571 B1 | 10/2005 | Srivastava | |
| 7,147,663 B1 * | 12/2006 | Berg et al. | 623/2.38 |
| 2001/0002445 A1 | 5/2001 | Vesely | |
| 2001/0007956 A1 | 7/2001 | Letac et al. | |
| 2001/0021872 A1 | 9/2001 | Bailey et al. | |
| 2002/0029014 A1 | 3/2002 | Jayaraman | |
| 2002/0032481 A1 | 3/2002 | Gabbay | |
| 2002/0042651 A1 | 4/2002 | Liddicoat | |
| 2002/0107565 A1 | 8/2002 | Greenhalgh | |
| 2002/0138138 A1 | 9/2002 | Yang | |
| 2003/0069492 A1 | 4/2003 | Abrams et al. | |
| 2003/0109924 A1 | 6/2003 | Cribier | |
| 2004/0029436 A1 | 2/2004 | Spenser et al. | |
| 2004/0093060 A1 | 5/2004 | Sequin et al. | |
| 2004/0097788 A1 | 5/2004 | Mourles et al. | |
| 2004/0111096 A1 | 6/2004 | Tu | |
| 2004/0117009 A1 | 6/2004 | Cali | |
| 2004/0122516 A1 | 6/2004 | Fogarty | |
| 2004/0138743 A1 | 7/2004 | Myers | |
| 2004/0167573 A1 | 8/2004 | Williamson | |
| 2004/0167620 A1 | 8/2004 | Ortiz | |
| 2004/0176840 A1 | 9/2004 | Langberg | |
| 2004/0186558 A1 | 9/2004 | Pavcnik | |
| 2004/0186563 A1 | 9/2004 | Lobbi | |
| 2004/0193261 A1 | 9/2004 | Berreklouw | |
| 2004/0210304 A1 | 10/2004 | Seguin et al. | |
| 2004/0210306 A1 | 10/2004 | Quijano | |
| 2004/0210307 A1 | 10/2004 | Khairkhahan | |
| 2004/0215333 A1 | 10/2004 | Duran | |
| 2004/0225353 A1 | 11/2004 | McGuckin, Jr. | |
| 2004/0225354 A1 | 11/2004 | Allen | |
| 2004/0225355 A1 | 11/2004 | Stevens | |
| 2004/0260390 A1 | 12/2004 | Sarac | |
| 2005/0010287 A1 | 1/2005 | Macoviak | |
| 2005/0021136 A1 | 1/2005 | Xie | |
| 2005/0033398 A1 | 2/2005 | Seguin | |
| 2005/0043757 A1 | 2/2005 | Arad | |
| 2005/0043790 A1 | 2/2005 | Seguin | |
| 2005/0049692 A1 | 3/2005 | Numamoto | |
| 2005/0049696 A1 | 3/2005 | Siess | |
| 2005/0055088 A1 | 3/2005 | Liddicoat | |
| 2005/0060029 A1 | 3/2005 | Le | |
| 2005/0065594 A1 | 3/2005 | Di Matteo | |
| 2005/0075584 A1 | 4/2005 | Cali | |
| 2005/0075712 A1 | 4/2005 | Biancucci | |
| 2005/0075717 A1 | 4/2005 | Nguyen | |
| 2005/0075719 A1 | 4/2005 | Bergheim | |
| 2005/0075724 A1 | 4/2005 | Svanidze | |
| 2005/0075725 A1 | 4/2005 | Rowe | |
| 2005/0075730 A1 | 4/2005 | Myers | |
| 2005/0075731 A1 | 4/2005 | Artof | |
| 2005/0096738 A1 | 5/2005 | Cali | |
| 2005/0113910 A1 | 5/2005 | Paniagua | |
| 2005/0131438 A1 | 6/2005 | Cohn | |
| 2005/0137683 A1 | 6/2005 | Hezi-Yamit et al. | |
| 2005/0137686 A1 | 6/2005 | Salahieh | |
| 2005/0137692 A1 | 6/2005 | Haug | |
| 2005/0137695 A1 | 6/2005 | Salahieh | |
| 2005/0137701 A1 | 6/2005 | Salahieh | |
| 2005/0143807 A1 | 6/2005 | Pavcnik | |
| 2005/0143809 A1 | 6/2005 | Salahieh | |
| 2005/0165477 A1 | 7/2005 | Anduiza | |
| 2005/0165479 A1 | 7/2005 | Drews | |
| 2005/0197695 A1 | 9/2005 | Stacchino | |
| 2005/0203549 A1 | 9/2005 | Realyvasquez | |
| 2005/0203614 A1 | 9/2005 | Forster | |
| 2005/0203618 A1 | 9/2005 | Sharkawy | |
| 2005/0228495 A1 | 10/2005 | Macoviak | |
| 2005/0234546 A1 | 10/2005 | Nugent | |
| 2005/0240200 A1 | 10/2005 | Bergheim | |
| 2005/0240262 A1 | 10/2005 | White | |
| 2006/0025854 A1 * | 2/2006 | Lashinski et al. | 623/1.25 |
| 2006/0025855 A1 * | 2/2006 | Lashinski et al. | 623/2.1 |
| 2006/0287717 A1 * | 12/2006 | Rowe et al. | 623/2.11 |

FOREIGN PATENT DOCUMENTS

| | | |
|---|---|---|
| DE | 195 46 692 | 6/1997 |
| DE | 198 57 887 | 7/2000 |
| DE | 199 07 646 | 8/2000 |
| DE | 10049812 | 4/2002 |
| DE | 10049813 | 4/2002 |

| | | | | | | |
|---|---|---|---|---|---|---|
| DE | 10049814 | 4/2002 | | WO | WO 01/64137 | 9/2001 |
| DE | 10049815 | 4/2002 | | WO | WO 01/97715 | 12/2001 |
| EP | 0 144167 | 6/1985 | | WO | WO 02/41789 | 5/2002 |
| EP | 0 597967 | 12/1994 | | WO | WO 02/43620 | 6/2002 |
| EP | 0 850607 | 7/1998 | | WO | WO 02/47575 | 6/2002 |
| EP | 1 057460 | 12/2000 | | WO | WO 02/036048 | 10/2002 |
| EP | 1 088529 | 4/2001 | | WO | WO 03/003949 | 1/2003 |
| EP | 1435879 | 7/2004 | | WO | WO 03/011195 | 2/2003 |
| EP | 1439800 | 7/2004 | | WO | WO 03/094793 | 11/2003 |
| EP | 1472996 | 11/2004 | | WO | WO 2004/058106 | 7/2004 |
| EP | 1570809 | 9/2005 | | WO | WO 2004/089250 | 10/2004 |
| FR | 2788217 | 7/2000 | | WO | WO 2004/089253 | 10/2004 |
| GB | 2056023 | 3/1981 | | WO | WO 2004/093728 | 11/2004 |
| SU | 1271508 | 11/1986 | | WO | WO 2004/105651 | 12/2004 |
| WO | WO 91/17720 | 11/1991 | | WO | WO 2005/002466 | 1/2005 |
| WO | WO 92/17118 | 10/1992 | | WO | WO 2005/004753 | 1/2005 |
| WO | WO 93/01768 | 2/1993 | | WO | WO 2005/009285 | 2/2005 |
| WO | WO 98/29057 | 7/1998 | | WO | WO 2005/011534 | 2/2005 |
| WO | WO 99/33414 | 7/1999 | | WO | WO 2005/011535 | 2/2005 |
| WO | WO 99/40964 | 8/1999 | | WO | WO 2005/023155 | 3/2005 |
| WO | WO 99/47075 | 9/1999 | | WO | WO 2005/027790 | 3/2005 |
| WO | WO 00/41652 | 7/2000 | | WO | WO 2005/046528 | 5/2005 |
| WO | WO 00/47139 | 8/2000 | | WO | WO 2005/046529 | 5/2005 |
| WO | WO 00/64380 | 11/2000 | | WO | WO 2005/048883 | 6/2005 |
| WO | WO 01/49213 | 7/2001 | | WO | WO 2005/096993 | 10/2005 |
| WO | WO 01/54625 | 8/2001 | | | | |
| WO | WO 01/62189 | 8/2001 | | * cited by examiner | | |

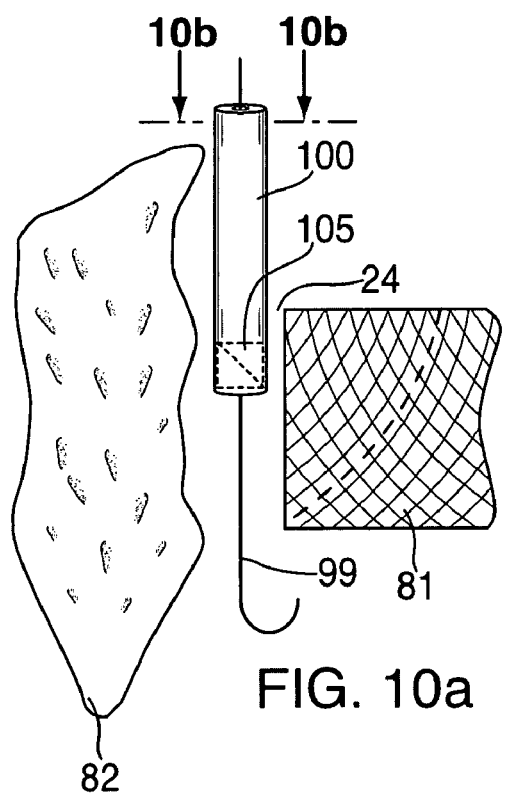
FIG. 10a
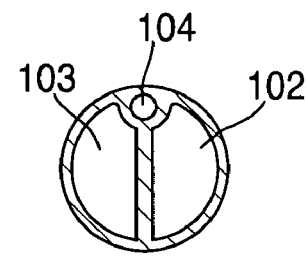
FIG. 10b
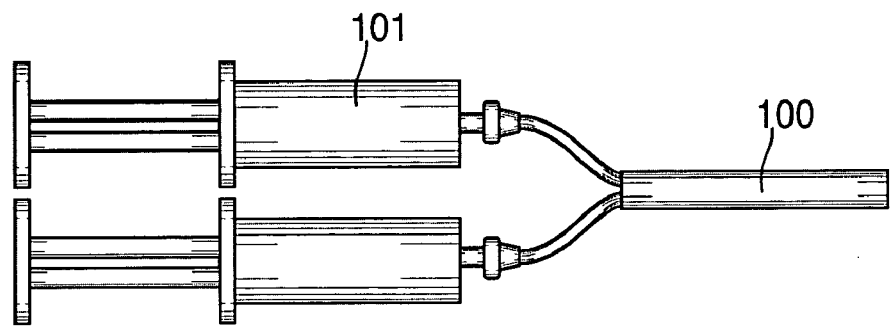
FIG. 10c
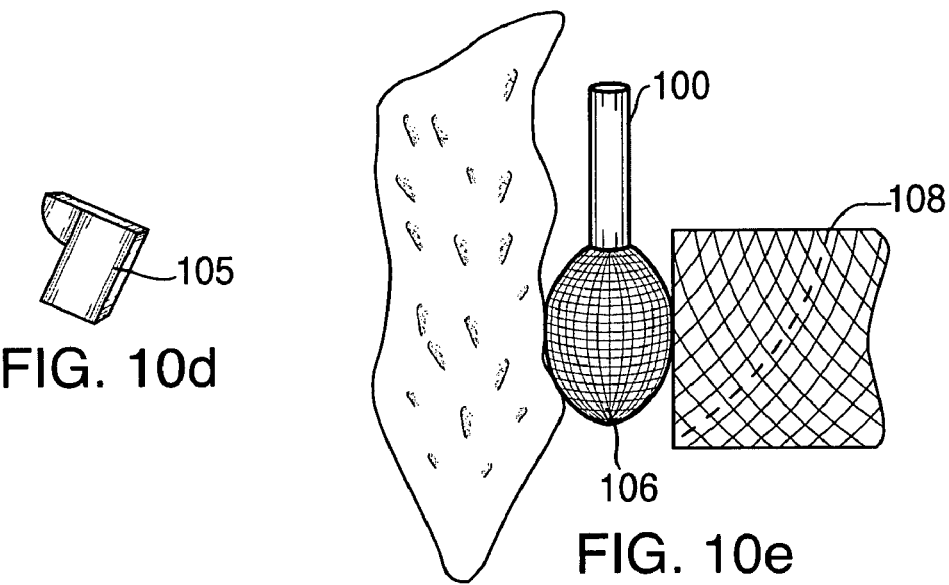
FIG. 10d
FIG. 10e

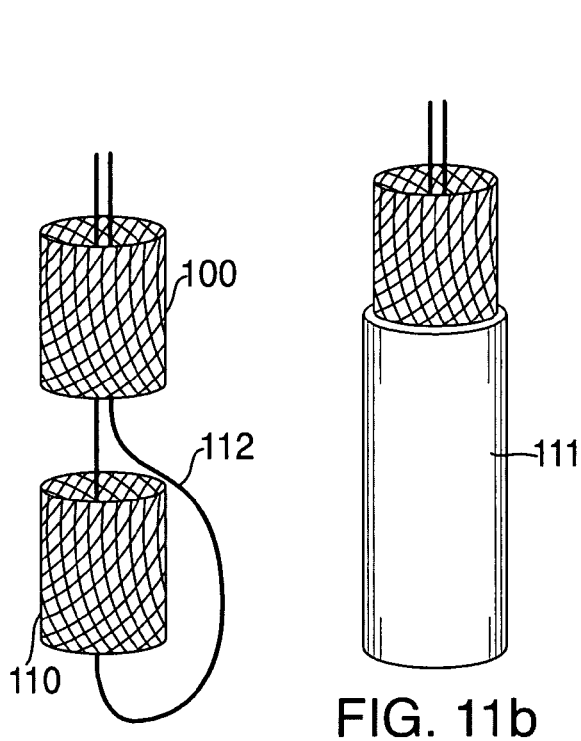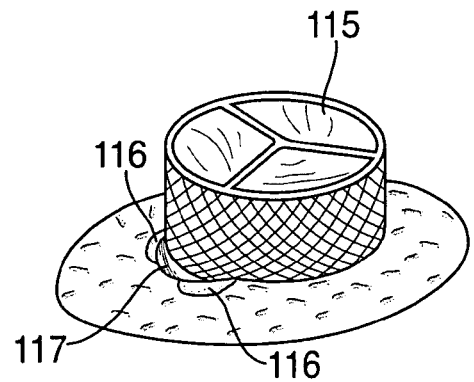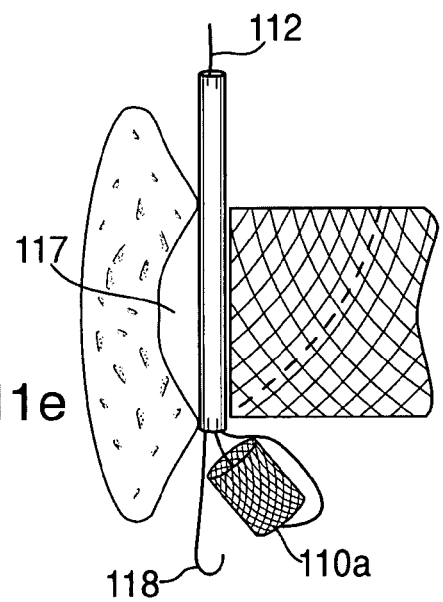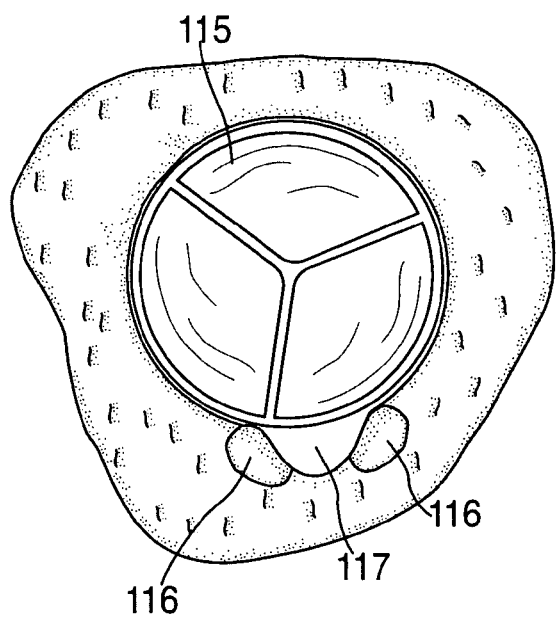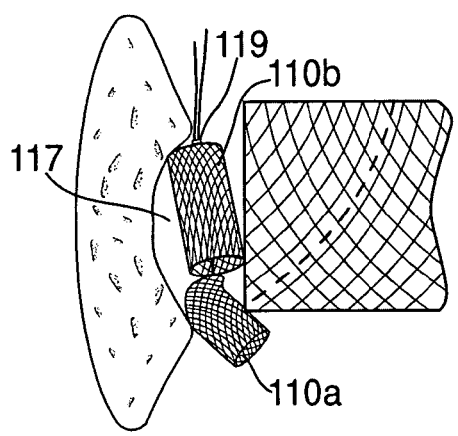
FIG. 11a
FIG. 11b
FIG. 11c
FIG. 11d
FIG. 11e
FIG. 11f

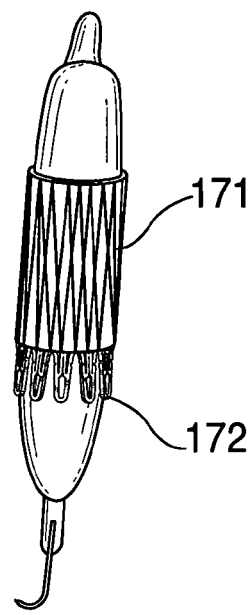
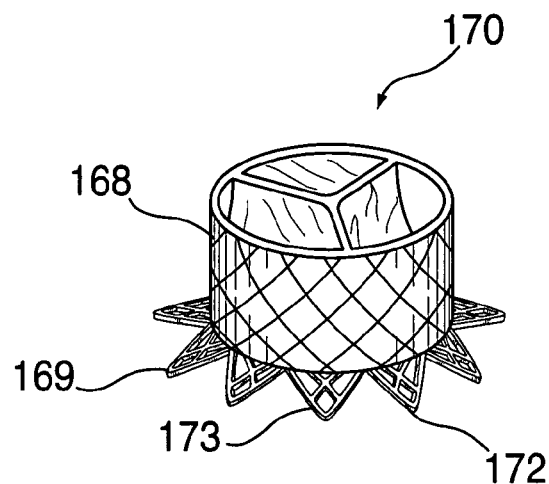
FIG. 17a
FIG. 17b
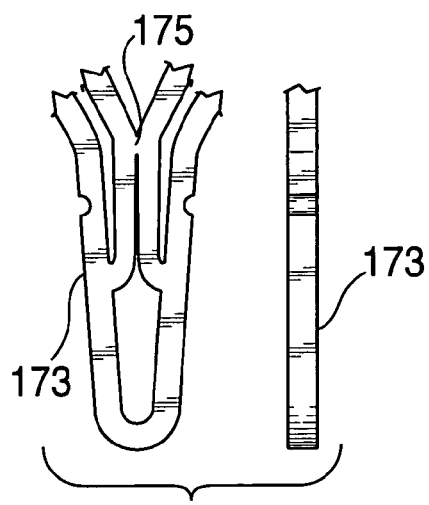
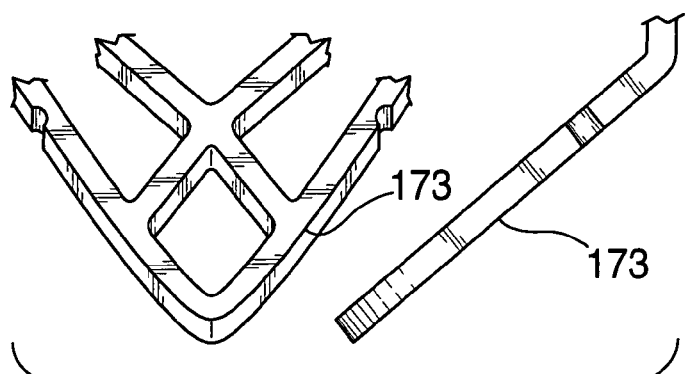
FIG. 17c
FIG. 17d
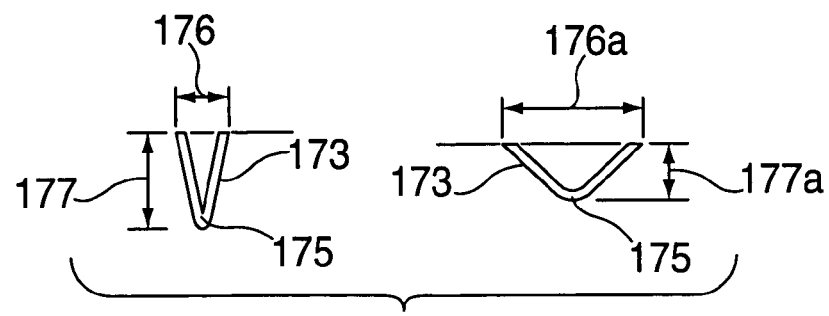
FIG. 17e

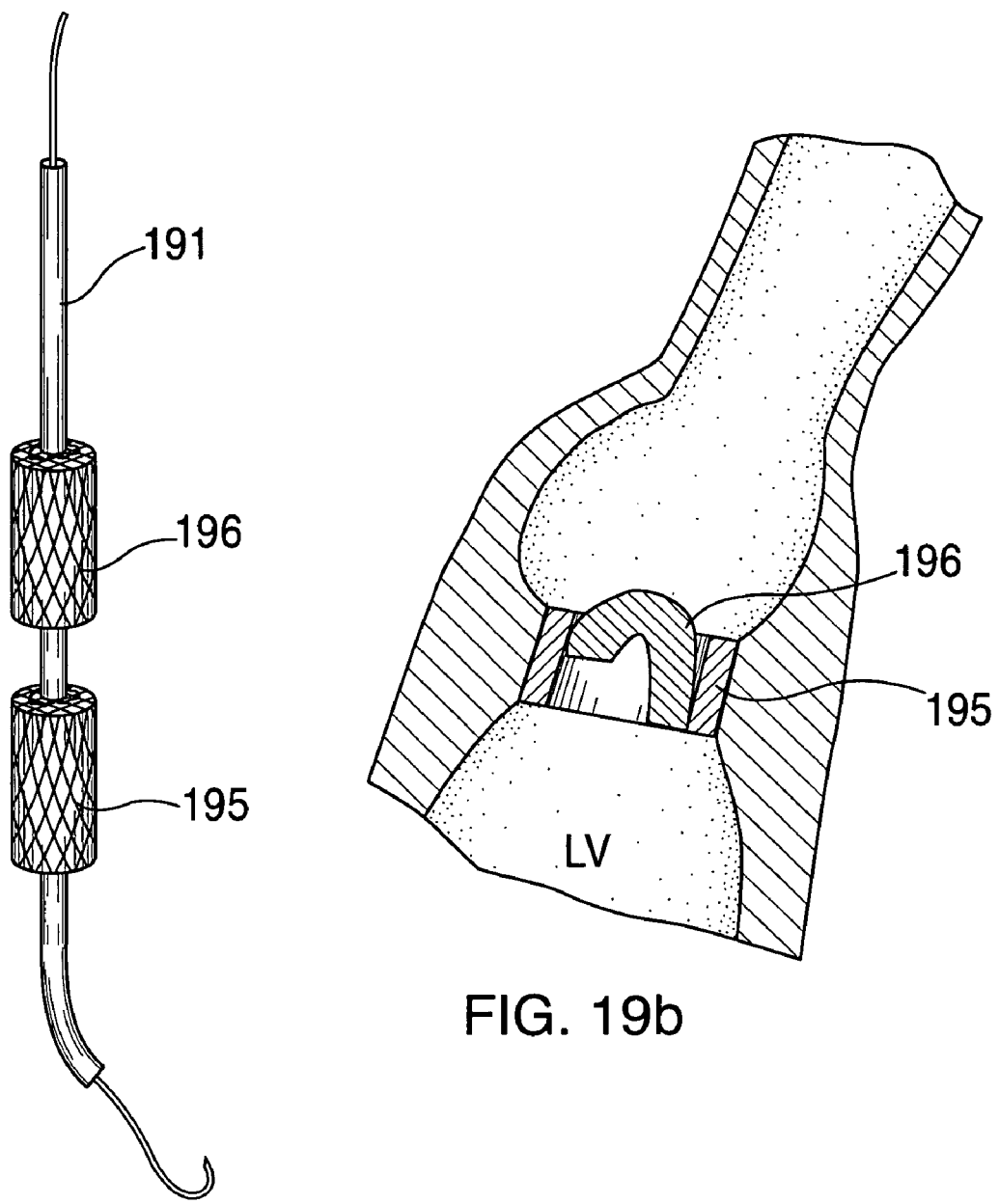
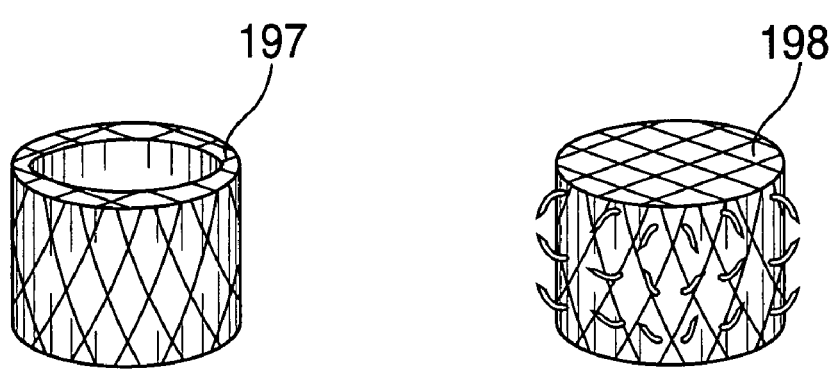
FIG. 19a
FIG. 19b
FIG. 19c
FIG. 19d

PARAVALVULAR LEAK DETECTION, SEALING, AND PREVENTION

FIELD OF THE INVENTION

The present invention relates to implantable devices. More particularly it relates to the prevention, detection, and repair of paravalvular leaks around cardiac valve prostheses.

BACKGROUND OF THE INVENTION

Cardiac valve implantation is well known in the art. Less well addressed is how to detect possible leaks between the valve and surrounding blood vessel, how to seal such leaks, or how to design the valve such that it automatically seals the leaks.

Machiraju in U.S. Pat. No. 5,554,184, entitled "HEART VALVE", describes a heart valve and a technique for effecting valve replacement or repair, which partially or completely replaces the mitral (or tricuspid) valve with an autologous graft from the pericardium, fascia lata or even the dura mater, or a bovine or porcine pericardial or other synthetic sheet material equivalent thereof, preferably in a configuration which substantially restores the original anatomy of the heart, including chordae tendineae attached to adjacent papillary muscles of the heart. Most preferably, a section of the patient's pericardium is cut to a shape including two leaflets, with each leaflet having a trabeculated tier of chordae tendineae terminating in a spear-shaped tab. The two leaflets are cut out as a single unit, and the two far ends are sutured together to yield a bileaflet valve having appended chordae and tabs.

Machiraju does not address leaks that can occur around the implanted valve.

Schreck in U.S. Pat. No. 6,454,799, entitled, "MINIMALLY-INVASIVE HEART VALVES AND METHODS OF USE", describes expandable heart valves for minimally invasive valve replacement surgeries. In a first embodiment, an expandable pre-assembled heart valve includes a plastically-expandable annular base having a plurality of upstanding commissure posts. A tubular flexible member including a prosthetic section and a fabric section is provided, with the prosthetic section being connected to the commissure posts and defining leaflets therebetween, and the fabric section being attached to the annular base. In a second embodiment, an expandable heart valve includes an annular tissue-engaging base and a subassembly having an elastic wireform and a plurality of leaflets connected thereto. The annular base and subassembly are separately stored and connected just prior to delivery to the host annulus. Preferably the leaflet subassembly is stored in its relaxed configuration to avoid deformation of the leaflets. The expandable heart valves may be implanted using a balloon catheter. Preferably the leaflets of the heart valves are secured to the commissure regions of the expandable stents using a clamping arrangement to reduce stress.

Schreck also does not address leaks that can occur around the implanted valve.

Amplatz in U.S. Pat. No. 6,638,257, entitled, "INTRAVASCULAR FLOW RESTRICTOR," describes an intravascular flow restrictor that comprises a braided tubular structure designed to be placed in the main pulmonary artery for limiting blood pressure in the lungs. The braided structure is designed to be collapsed for placement in a delivery catheter, but when it is ejected from the delivery catheter, it assumes a substantially larger diameter disk shaped device having one or more longitudinal channels or passways therethrough.

Amplatz also does not address leaks that can occur around the implanted valve. In addition, Amplatz's braided structures are of a shape and size not appropriate for paravalvular leak detection and sealing. Their geometry is designed for the conditions of the transceptal hole and not appropriate for valve leakage.

Spenser et al. in U.S. Patent Application No. 20030153974, entitled "IMPLANTABLE PROSTHETIC VALVE", describe a prosthesis device suitable for implantation in body ducts. The device comprises a support stent bring comprised of a deployable construction adapted to be initially crimped in a narrow configuration suitable for catheterization through a body duct to a target location and adapted to be deployed by exerting substantially radial forces from within by means of a deployment device to a deployed state in the target location, the support stent bring provided with a plurality of longitudinally rigid support beams of fixed length, and (2) a valve assembly comprising a flexible conduit having an inlet end and an outlet, made of pliant material attached to the support beams providing collapsible slack portions of the conduit at the outlet. When flow is allowed to pass through the valve prosthesis device from the inlet to the outlet, the valve assembly is kept in an open position, whereas a reverse flow is prevented as the collapsible slack portions of the valve assembly collapse inwardly to provide blockage to the reverse flow.

Spenser et al. also do not address leaks that can occur around the implanted valve.

With regard to the general topic of prosthetic valves, implantation is currently done either through open heart surgery or by use of newer percutaneous methods, some of which are described in the patents mentioned above. With both methods paravalvular leaks are a known side effect. One way to approach the leak problem is to identify the leak location and repair it. Another approach is to equip the prosthesis with means to prevent the leak ("self-sealing" prosthesis). Both these approaches are encompassed by the present invention.

Percutaneous introduction of medical devices is a preferred surgical procedure for it involves making only a very small perforation in the patient's skin (usually in the groin or armpit area) under local anesthetic sedation. In contrast, surgical placement involves a large chest, surgical incision and requires general anesthesia, to expose a large portion of a patient's thoracic region. Percutaneous introduction is therefore considered safer and less invasive.

Percutaneous introduction of a leak detection and repair device or of a self-sealing valve resembles other known interventional cardiologic procedures. The percutaneous deployment procedure and device has an impact on several parameters of the product design, some of which are explained hereinafter.

In summary, the present invention provides new concepts of percutaneous paravalvular repair, including means for identifying the leak location, repair techniques, and means for leak prevention that can be engineered into the prosthesis valve itself.

SUMMARY OF THE INVENTION

In accordance with a preferred embodiment of the present invention, a catheter-delivered device is provided for locating cavities occurring between a prosthetic valve and the wall of the body vessel where the valve is implanted, the cavities producing paravalvular leaks during diastole. The device comprises at least one of a plurality of flexible wires, the wire having attached to it a balloon, wherein the balloon is pulled by the leak through the cavity and wherein the wire then serves to mark the cavity location.

Furthermore, in accordance with another preferred embodiment of the present invention, a spacing element is provided to maintain the wires adjacent to the wall of the body vessel.

There is thus also provided in accordance with a preferred embodiment of the present invention, a catheter-delivered stent for sealing cavities occurring between a prosthetic valve and the wall of the body vessel where the valve is implanted, the cavities producing paravalvular leaks during diastole. The stent, which is delivered via a guidewire to the cavity and held in place in the cavity by friction, comprises a support structure and an impermeable membrane, the membrane preventing the passage of fluids through the stent, thereby sealing the cavity.

Furthermore, in accordance with another preferred embodiment of the present invention, the sealing stent is balloon-expandable and the membrane comprises a tab spring-hinged to the inside of the stent lumen and sized to occlude the lumen when closed. The tab is held open by the stent balloon during insertion and springs closed when the balloon is removed after the stent is expanded.

Furthermore, in accordance with another preferred embodiment of the present invention, the sealing stent is self-expandable, wherein the membrane is a material covering at least one end of the stent.

Furthermore, in accordance with another preferred embodiment of the present invention, the stent is comprised of shape memory material.

Furthermore, in accordance with another preferred embodiment of the present invention, the material is nitinol.

Furthermore, in accordance with another preferred embodiment of the present invention, the stent is covered on its external walls with hooks comprised of shape memory material and which extend, upon insertion of the stent, into adjacent body vessel walls.

Furthermore, in accordance with another preferred embodiment of the present invention, the distal end of the stent-delivery catheter is substantially perpendicular to the wall of the vessel at a point inside the cavity and the stent guidewire terminates in an anchoring mechanism that is inserted through the catheter and into the vessel wall, anchoring itself in the vessel wall and providing greater anchorage for the stent.

Furthermore, in accordance with another preferred embodiment of the present invention, the anchoring mechanism is a hook comprised of shape memory material that is compressed for catheter delivery into the vessel wall, whereupon the hook extends out, anchoring the guidewire into the vessel wall.

Furthermore, in accordance with another preferred embodiment of the present invention, the anchoring mechanism is a threaded point that is threaded into the vessel wall anchoring the guidewire into the vessel wall.

Also provided in accordance with a preferred embodiment of the present invention, is a device for sealing cavities occurring between a prosthetic valve and the wall of the body vessel where the valve is implanted, the cavities producing paravalvular leaks during diastole. The device comprises a first guidewire threaded through the cavity, a second guidewire slidably coupled to the first guidewire and inserted such that the slidable coupling is moved to a desired point in the cavity, a first catheter inserted over the first guidewire to the point in the cavity, a second catheter inserted over the second guidewire to the desired point in the cavity, a first component of a two-component biological adhesive inserted through the first catheter to the desired point, a second component of the two-component adhesive inserted through the second catheter to the desired point, the two components thereby mixing to form a plug that seals the cavity.

Furthermore, in accordance with another preferred embodiment of the present invention, the device is adapted to apply an adhesive with more than two components.

Furthermore, in accordance with another preferred embodiment of the present invention, instead of two guidewires and two catheters, a single catheter and guidewire are used for delivery, with the catheter comprising two lumens, each lumen providing delivery for one of the two-component adhesive components, and the catheter terminates in a mixer that forces the components to mix when they exit the catheter in the cavity, thereby creating the plug that seals the cavity.

Furthermore, in accordance with another preferred embodiment of the present invention, instead of two-component adhesive components being delivered via the catheters, a radiation-cured adhesive is delivered via one of the catheters and a radiation source is delivered via the other catheter, wherein the radiation source is applied to the adhesive to create the plug in the cavity.

Also provided in accordance with a preferred embodiment of the present invention is a catheter-delivered assembly for sealing cavities occurring between a prosthetic valve and the wall of the body vessel where the valve is implanted, the cavities producing paravalvular leaks during diastole. The assembly is delivered via guidewire to the cavity and comprises two sealing stents connected by a suture, the suture running back up the catheter, the sealing stents comprising a stent structure and sealing membrane. One stent of the assembly is inserted underneath the cavity and the other stent is inserted inside the cavity, the membranes preventing the passage of fluids through the stent, thereby sealing the cavity and each stent helping anchor the other in place.

There is thus also provided in accordance with a preferred embodiment of the present invention, a prosthetic valve with integrated sealing ring attached to the outside wall, the ring having a circumference greater than that of the valve and elastically conforming to seal cavities between the valve and the wall of the body vessel where the valve is implanted, the cavities producing paravalvular leaks during diastole.

Furthermore, in accordance with another preferred embodiment of the present invention, the ring comprises a balloon.

Furthermore, in accordance with another preferred embodiment of the present invention, the ring comprises a plurality of spring-wire tabs mounted adjacent to one another around the circumference of the valve and covered with an impermeable membrane. The tabs are folded against the body of the valve during catheter delivery, and, upon egress from the catheter, the tabs spring out to form the sealing ring.

Furthermore, in accordance with another preferred embodiment of the present invention, the ring comprises a plurality of impermeable tabs mounted adjacent to one another around the circumference of the valve, and further comprises a balloon under the tabs. The tabs are folded down on the deflated balloon during catheter delivery, and, upon egress from the catheter, the balloon is inflated, thereby opening the tabs to form the sealing ring.

Furthermore, in accordance with another preferred embodiment of the present invention, the ring comprises a plurality of impermeable tabs mounted adjacent to one another around the circumference of the valve, each tab spring-hinged to the valve. The tabs are folded against the body of the valve during catheter delivery, and, upon egress from the catheter, the tabs spring out to form the sealing ring.

Furthermore, in accordance with another preferred embodiment of the present invention, the ring comprises at least one of a plurality of flexible, self-expanding sealing elements comprised of self-expanding mesh covered with an impermeable membrane.

Furthermore, in accordance with another preferred embodiment of the present invention, the ring comprises at least one of a plurality of flexible, self-expanding sealing elements comprised of self-expanding mesh covered with an impermeable membrane.

Furthermore, in accordance with another preferred embodiment of the present invention, the sealing ring comprises modified struts of the stent, the modification comprising geometrical constraints that, upon expansion of the stent, cause the struts to bend out from the stent body, thereby creating the sealing ring.

There is thus also provided in accordance with a preferred embodiment of the present invention, a prosthetic valve with integrated sealing means, the sealing means comprising sutures attached around the perimeter of the valve and extending back out of the body. Patches can be pushed down the sutures and attached to the point where the suture is attached to the valve, thereby sealing any cavity existing between the valve and the wall of the body vessel where the valve is implanted, the cavities producing paravalvular leaks during diastole.

There is thus also provided in accordance with a preferred embodiment of the present invention, a catheter-delivered prosthetic valve with integrated sealing means, the sealing means comprising an elastic stent that is first deployed and inside which the valve is deployed. The elastic stent seals any cavity existing between the valve and the wall of the body vessel where the valve is implanted, the cavities producing paravalvular leaks during diastole.

There is thus also provided in accordance with a preferred embodiment of the present invention, a method for locating cavities between an implanted prosthetic valve and the wall of the body vessel where the valve is implanted, the cavities producing paravalvular leaks during diastole. The method comprises:

inserting a balloon mounted on a flexible wire next to the valve, wherein the balloon is pulled by the leak through the cavity and wherein the wire then serves to mark the cavity location.

There is thus also provided in accordance with a preferred embodiment of the present invention, a method for sealing cavities between an implanted prosthetic valve and the wall of the body vessel where the valve is implanted, the cavities producing paravalvular leaks during diastole. The method comprises:

inserting an impermeable stent into the cavity, whereby the stent seals the cavity.

There is thus also provided in accordance with a preferred embodiment of the present invention, a method for sealing cavities between an implanted prosthetic valve and the wall of the body vessel where the valve is implanted, the cavities producing paravalvular leaks during diastole. The method comprises:

inserting a first guidewire into the cavity;

running a loop attached to a second guidewire over the first guidewire to a point inside the cavity;

injecting one component of a two-component adhesive through a catheter over the first guidewire to the cavity; and injecting the second component of the two-component adhesive through a catheter over the second guidewire to the cavity, wherein the components combine to create an adhesive plug that seals the cavity.

Furthermore, in accordance with another preferred embodiment of the present invention, instead of the first adhesive component, a radiation-cured adhesive is injected and instead of the second adhesive component a radiation source is applied, thereby creating the adhesive plug.

Furthermore, in accordance with another preferred embodiment of the present invention, only one guidewire is used and the two components are inserted via separate lumens within a single catheter over the guidewire.

There is thus also provided in accordance with a preferred embodiment of the present invention, a method for providing integrated sealing capability in an implanted prosthetic valve and the wall of the body vessel where the valve is implanted, the cavities producing paravalvular leaks during diastole. The method comprises:

providing an expandable elastic ring around the outside of the valve; and expanding the ring, wherein the ring seals any cavities.

There is thus also provided in accordance with a preferred embodiment of the present invention, a method for sealing cavities between an implanted prosthetic valve and the wall of the body vessel where the valve is implanted, the cavities producing paravalvular leaks during diastole. The method comprises:

inserting a sealing stent at the distal end of the cavity; and inserting a second sealing stent attached to the first stent into the cavity.

BRIEF DESCRIPTION OF THE FIGURES

To better understand the present invention and appreciate its practical applications, the following Figures are provided and referenced hereafter. It should be noted that the Figures are given as examples only and in no way limit the scope of the invention as defined in the appended claims. Like components are denoted by like reference numerals.

FIGS. 10a to 10e illustrate a catheter, in accordance with another preferred embodiment of the present invention, that inserts a two-component biological glue into a balloon in order to block a paravalvular leak.

FIGS. 11a to 11f illustrate a device and procedure, in accordance with another preferred embodiment of the present invention, for blocking a paravalvular leak using two connected sealing stents.

FIGS. 17a to 17e illustrate a valve device, in accordance with another preferred embodiment of the present invention, where the stent is adapted such that when expanded, a portion of the stent is forced to protrude radially, thereby blocking possible leaks.

FIGS. 19a to 19d depict a procedure, in accordance with another preferred embodiment of the present invention, the procedure comprising two stages: first, insertion of a stent that includes an outer sealing layer; and second, insertion of a prosthetic valve through the stent.

DETAILED DESCRIPTION OF THE INVENTION

Figure 1:
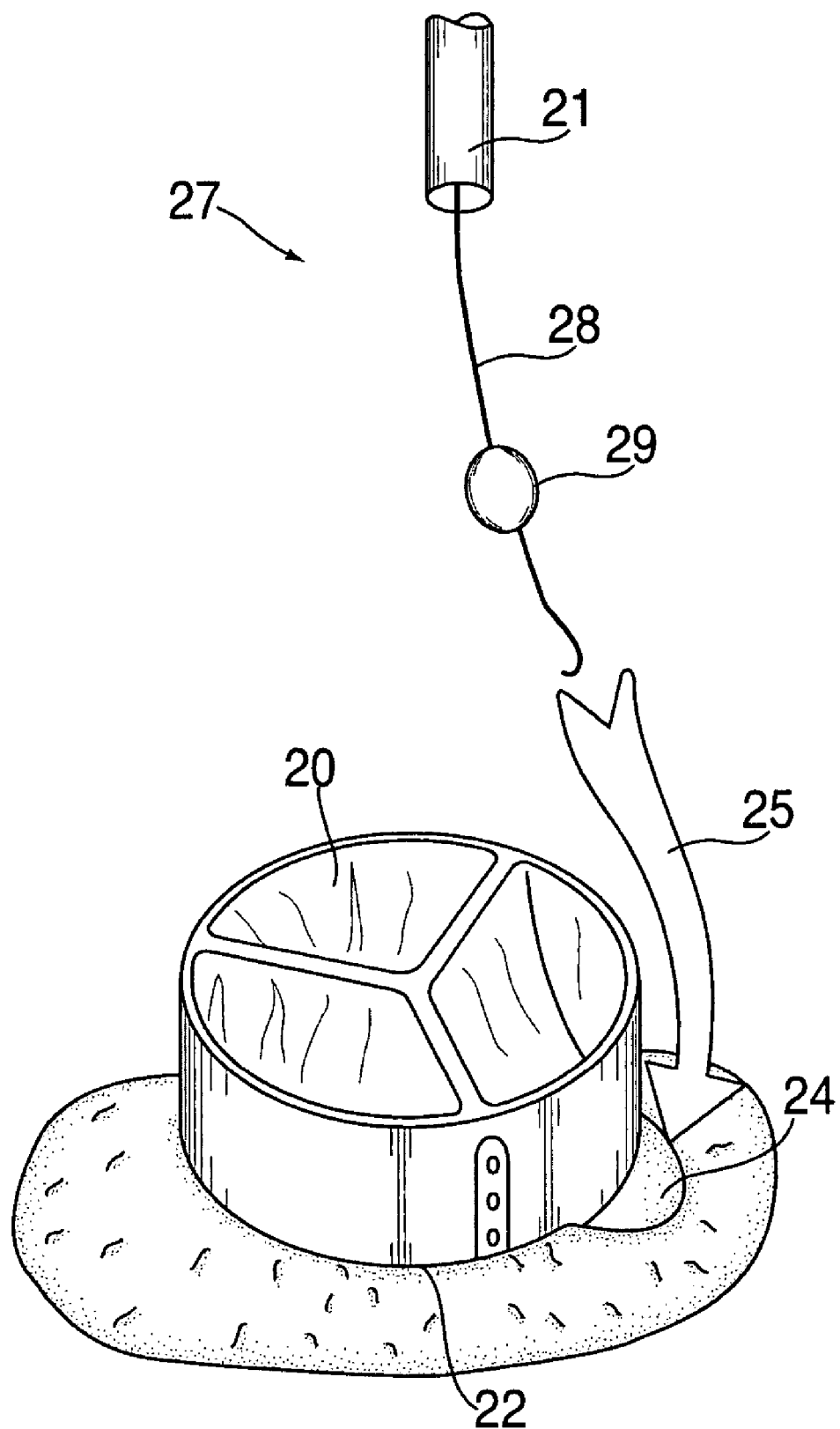
FIG. 1 illustrates an implanted valve with a cavity creating a paravalvular leak and a device, in accordance with a preferred embodiment of the present invention, comprising a soft guidewire with an inflatable balloon and designed to identify the exact location of the paravalvular leak.

The present invention provides methods and apparatuses for substantially reducing or effectively eliminating the deleterious effects of paravalvular leaks in prosthetic valves. More specifically, it enables locating, sealing, and preventing paravalvular leaks using both dedicated and integrated (with the valve) means.

While the present invention is particularly suited for prosthetic heart valve leaks, such as a prosthetic aortic valve, it can also be applied to other leakage problems such as in other blood vessels, a septum, or other body lumens. Similarly, while the prosthetic valve described herein are tricuspid valves, it could be another type of valve as well.

A main aspect of the present invention is the introduction of several novel designs and methods for locating paravalvular leaks in prosthetic valves.

Another main aspect of the present invention are several novel designs for sealing paravalvular leaks detected in prosthetic valves.

Another main aspect of the present invention are several novel designs for modifying percutaneous prosthetic valves to automatically seal paravalvular leaks when the valve is implanted.

Another main aspect of the present invention is a novel design that automatically seals paravalvular leaks when the valve is implanted without requiring valve modification.

Another main aspect of the present invention is the disclosure of several novel designs for modifying percutaneous prosthetic valves to enable sealing of paravalvular leaks after the valve is implanted.

For locating paravalvular leaks, the present invention provides several designs comprising catheter-delivered balloons mounted on flexible guidewires. The balloons are delivered to a point near the valve. When regurgitation (leaking) occurs during diastole, the balloons are drawn into the leak-producing cavities occurring between the valve and the wall of the blood vessel, thereby providing a means to deliver means for sealing the leak.

For sealing paravalvular leaks, the present invention provides several designs including sealing stents, and multi-component and radiation-cured adhesive compounds.

Sealing stents are crimped stents that are delivered to the leak location, expanded, and anchored in place. The stents are designed to block flow, thereby sealing the leak. Several innovations are provided for these operations.

Delivery of the sealing stent is via a guidewire that is anchored in the wall of the blood vessel at the leak location. The anchoring means can be a hook, for example a multi-headed hook composed of a shape memory alloy, such as nickel titanium (also known as nitinol), which is crimped at low temperature for delivery. The anchoring means expands back to its original shape due to the higher temperature of the blood vessel wall at its deployment point, thereby anchoring itself into the blood vessel wall.

Another anchoring means is for the guidewire to be terminated in a screw, which can be threaded into the blood vessel wall.

Once delivered to the leak location via the guidewire, the sealed stent is expanded. This can be done by another agent, such as a balloon, or by making the stent self-expanding. In the case of balloon inflation, the stent is crimped around the deflated balloon prior to insertion in the delivery catheter. Upon delivery the balloon is inflated, thereby expanding the stent, and then the balloons can be deflated and withdrawn. In the case of the self-expanding stent, the stent is preferably built from a shape memory alloy, such as nickel titanium (also known as nitinol), which can be crimped at low temperature for delivery, expanding back to its original shape due to the higher body temperature at the deployment site. Alternatively the self-expanding stent can be a metallic stent comprised of a physiologically acceptable metal such as stainless steel or an alloy such as nitinol, which is compressed or wound on a delivery, catheter or device. When the stent is released from the delivery catheter or device, it expands.

The sealing stent is held in place by friction. Additional holding force can be obtained by adding hooks around the perimeter of the stent, such as self-expanding hooks made of shape memory alloy.

The expanded stent includes an internal element that seals the stent's own lumen, preventing flow through the stent and thereby sealing the cavity causing the leak. Examples of internal sealing elements include a spring-hinged flap inside the stent lumen that opens upon stent expansion or, in the case of the self-expanding stent, a membrane covering one or both openings of the stent.

In some cases, it may be preferred to use two sealing stents. In this embodiment, the two stents are connected in series by a suture. The delivery catheter is extended through the top of the cavity and out the bottom of the cavity to deploy one of the sealing stents and then, together with the stents' guide wire, retracted. This pulls the deployed stent back until it catches in the bottom of the cavity. The catheter is further retracted, and the second stent is deployed into the cavity. The catheter is further retracted and the second stent is pulled back, catching it (from the bottom) in the top of the cavity.

An alternative sealing element to the sealing stent is a biological adhesive compound that can be delivered to the cavity via catheter. In such a case, two catheters are brought to the leak location. The catheters are used in one of the following ways: to deliver two adhesive components that, when mixed, harden to form an adhesive sealing plug, or to deliver a radiation-cured adhesive and the cure source, for example an ultra-violet light source, to produce an adhesive sealing plug.

In both sealing element designs there is a need to bring the distal catheter ends in close proximity to one another, for proper mixing or curing, at the leak point. This is accomplished as follows: a first catheter is used to insert the leak detector guidewire mentioned above. A second guidewire is fitted with a loop, and the loop is run over the first guidewire until it reaches the leak location. The respective cathethers are then slid over their guidewires to meet at the leak location, thereby providing egress for applying the bi-component adhesive or radiation-cured adhesive.

Another delivery design for a bi-component adhesive utilizes a single catheter run over the leak detection guidewire. The catheter has three lumens: one to track the guidewire and one for each adhesive component. A mixing means at the distal end of the catheter mixes the components at the leak location to form the sealing plug.

In other embodiments of the present invention, leak sealing means are integrated into the valve as an impermeable ring that, when the valve is implanted, adaptively seals any gaps between the valve and the surrounding lumen.

In one embodiment of such a self-sealing valve, the ring is deflated for delivery and then inflated for sealing.

In another self-sealing valve embodiment, the ring is a sponge-like material that is compressed for delivery and then expands for sealing.

In another self-sealing valve embodiment, the ring comprises a set of flaps that are closed for delivery and are opened either by balloon inflation, by the geometry of their connection to the valve, or by spring-action.

In another self-sealing valve embodiment, the ring comprises a set of self-expanding tubes.

In another self-sealing valve embodiment, the ring comprises struts of the valve's stent that are geometrically constrained to bend and enlarge their final diameter in respect to the main stent geometry when expanded from the crimped form In another embodiment where sealing means are built into the valve, a set of filament pairs are attached around the valve and feed back to the delivery catheter ingress. When a paravalvular leak is detected, impermeable patches of a material such as pericardium are threaded onto the local filament pair and pushed down to the leak location where they are tied off in place.

In another embodiment of the present invention, a sealing stent is first inserted into the lumen, and then the valve is inserted inside the sealing stent.

The aforementioned embodiments as well as other embodiments, manufacturing methods, different designs and different types of devices are discussed with reference to the drawings. Note that the drawings are only given for the purpose of understanding the present invention and presenting some preferred embodiments of the present invention. The drawings are not meant to limit the scope of the present invention as defined in the appended claims.

FIG. 1 illustrates a simple leak detector 27 in accordance with a preferred embodiment of the present invention. Leak detector 27 detects a leak between general tricuspid implantable prosthesis valve 20 and the aortic annulus 22. Leak detector 27 will typically be used together with leak sealing devices, like those described later in this specification.

A cavity 24 exists between the perimeter of valve 20 and aortic annulus 22. The cavity could have any number of causes, including calcification or other irregularities in the aortic annulus 22 that prevent proper sealing between the valve 20 and the annulus 22. The cavity will cause regurgitation (leaking) during diastole, characterized by blood flowing 25 from the aorta into the left ventricle. Leak detector 27, is delivered through catheter 21 to a position above valve 20. Leak detector 27 comprises a soft guide wire 28 on which is mounted inflatable balloon 29, which is inflated after leak detector 27 has been passed through catheter 21. Guidewire 28 is soft enough that during diastole inflated balloon 29 is drawn into the regurgitation flow and lodges in cavity 24 in between valve 20 and annulus 22.

Figure 2A:
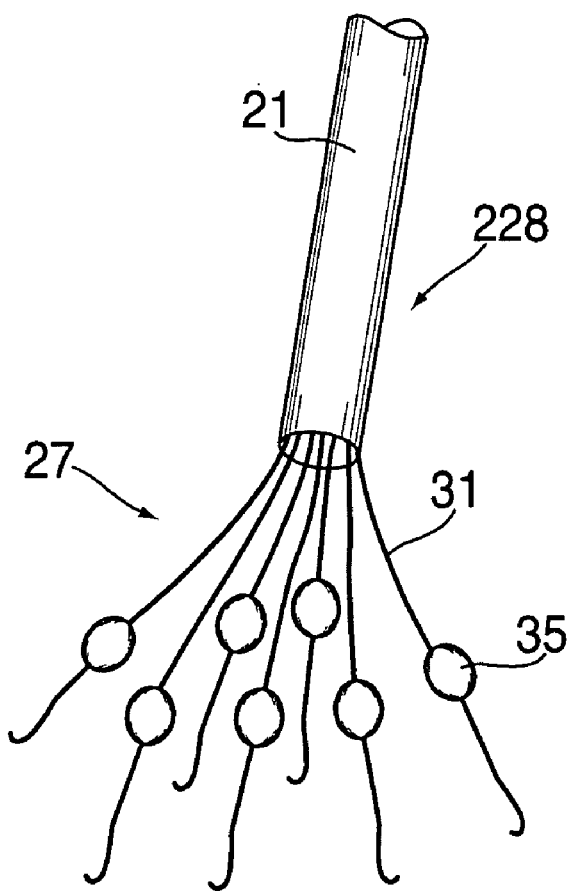
FIGS. 2a and 2b depict a plurality of balloons on soft guidewires, in accordance with another preferred embodiment of the present invention, designed to identify paravalvular leaks around an implanted valve.
Figure 2B:
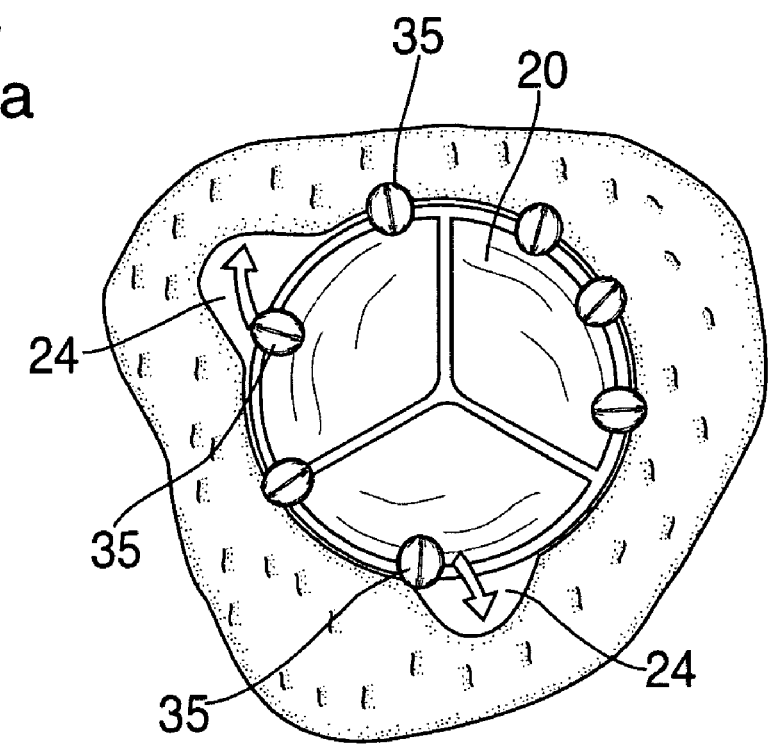

FIGS. 2a and 2b depict a multiple leak detector 228 that is similar to leak detector 27 of FIG. 1 but which comprises a plurality of soft guidewires 31 rather than just the single guidewire 28 of detector 27. On each guidewire 31 is mounted a balloon 35. FIG. 2b is a top view showing valve 20 during diastole. Two cavities 24 cause a flow of blood, which pulls the balloon 35 closest to each cavity 24 into that cavity while remaining balloons 35 stay stationary. At this point, cavity 24 locations can be determined and marked and the cavities repaired.

Figure 3:
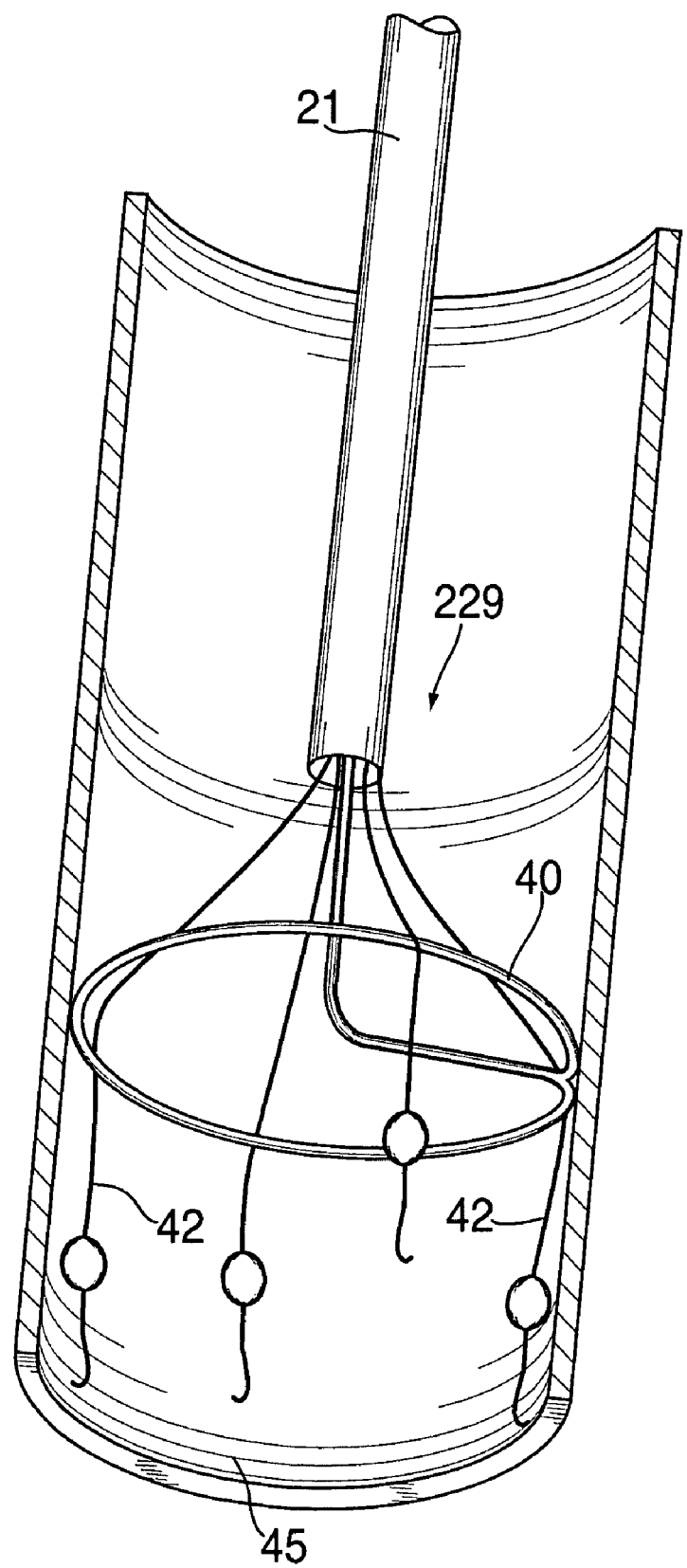
FIG. 3 illustrates a plurality of balloons on soft guidewires and kept along the perimeter of the blood vessel by a ring, in accordance with another preferred embodiment of the present invention, designed to identify paravalvular leaks around an implanted valve.

FIG. 3 illustrates an annular-configured leak detector 229, which incorporates an adaptation that can be used to force wire(s) 40 of leak detector 27 or multiple-leak detector 228 (implementation shown) to remain close to aortic wall 45 rather than being allowed to drift to the center of the aorta. The advantage of this adaptation is that, in the case of detectors 27 and 228, if there is a central leak in valve 20, a balloon near the center of the aorta might be drawn into the central leak instead of to the paravalvular cavity, thereby indicating a false paravalvular leak. Spacing ring 40 is a compressible wire ring that pops open after catheter 21 delivery. Guidewire(s) 42 are distributively attached to the external edge of ring 40 and are thereby held by the ring against the aortic wall 45.

Figure 4A:
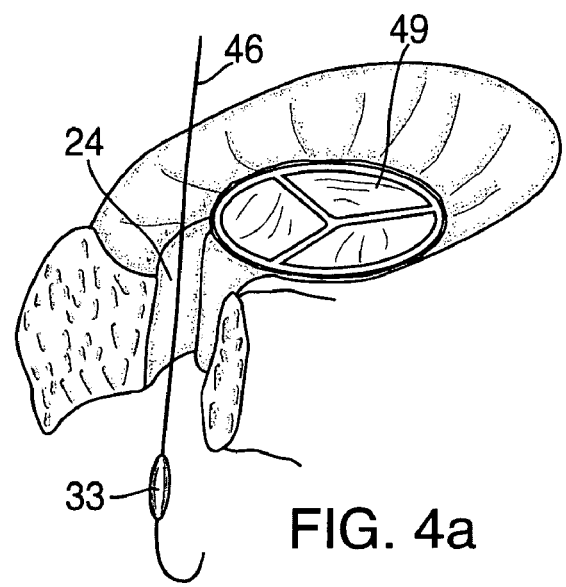
FIGS. 4a to 4c depict the process, in accordance with another preferred embodiment of the present invention, of inserting a sealing stent over a guidewire to close a paravalvular leak.
Figure 4B:
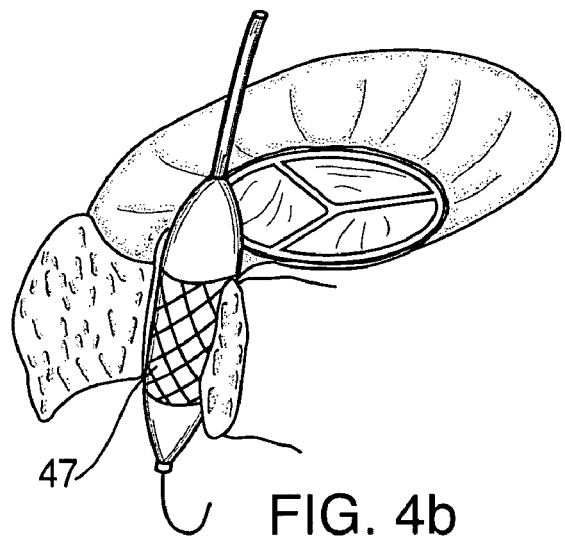
Figure 4C:
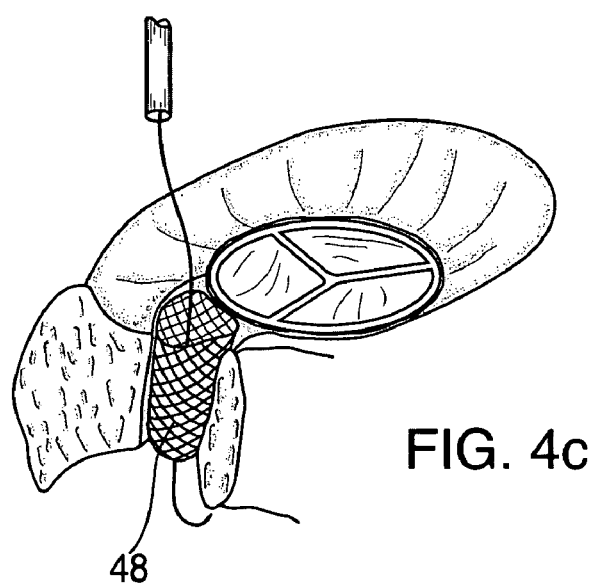

FIGS. 4a to 4c depict an implantable valve 49 deployed in the native aortic valve position, creating a cavity 24, which causes paravalvular regurgitation (leak) during diastole. In FIG. 4a, guidewire 46, which can be a leak detection device like those shown in FIGS. 1, 2, and 3, is inserted through cavity 24. Balloon 33 is deflated. In FIG. 4b, a balloon-expandable sealing stent (stent with an impermeable membrane that prevents the passage of fluids through the stent), is catheter-deployed over guidewire 46. Balloon 33 is inflated, causing balloon-expandable sealing stent 47 to be expanded, thereby sealing cavity 24 and stopping the paravalvular leak. FIG. 4c shows a similar leak repair with the difference that a self-expanding sealing stent 48 is used, and therefore balloon inflation is not required. The sealing stents 47 and 48 are anchored by friction between themselves and the surrounding aortic annulus. Means for providing stronger anchoring for sealing stents are described later in this specification.

Figure 5A:
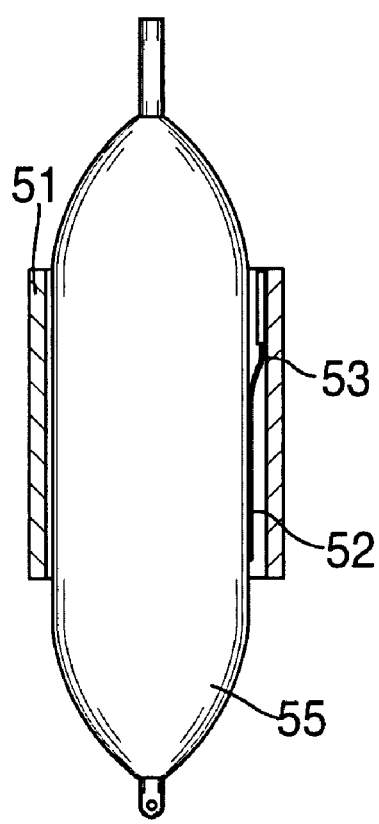
FIGS. 5a to 5d depict several types of sealing stents, in accordance with another preferred embodiment of the present invention.
Figure 5B:
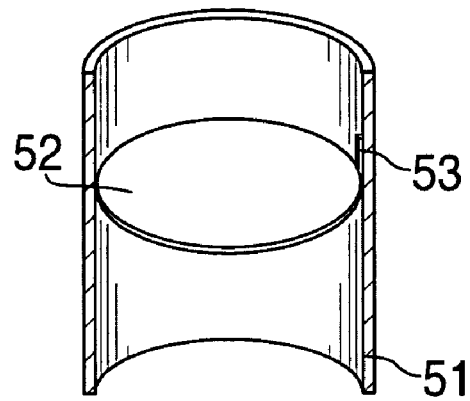

FIGS. 5a and 5b illustrate an embodiment of a balloon-expandable sealing stent (such as that used in FIG. 4b) in accordance with another preferred embodiment of the present invention. The outer part 51 of the stent is made of a material that can be reshaped by plastic deformation. Sealing element 52, comprising an impermeable membrane, is connected to the inside wall of outer part 51 by spring hinge 53. The balloon-expandable sealing stent 47 is crimped on balloon 55. Once balloon 55 has reached cavity 24, the balloon is inflated, thereby expanding the sealing stent (FIG. 5a). Balloon 33 is then deflated, whereupon (FIG. 5b) sealing element 52 is forced by spring 53 to close and seal the lumen of the stent.

Figure 5C:
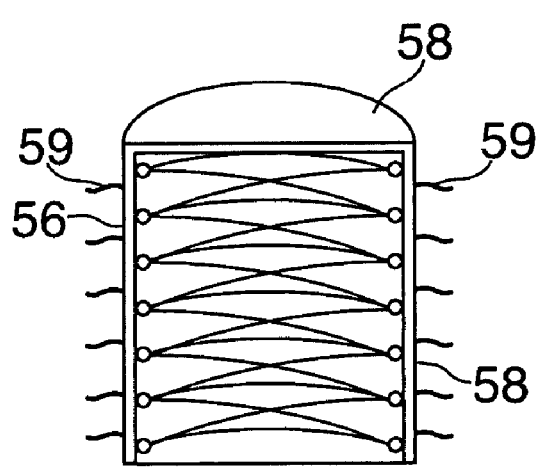
Figure 5D:
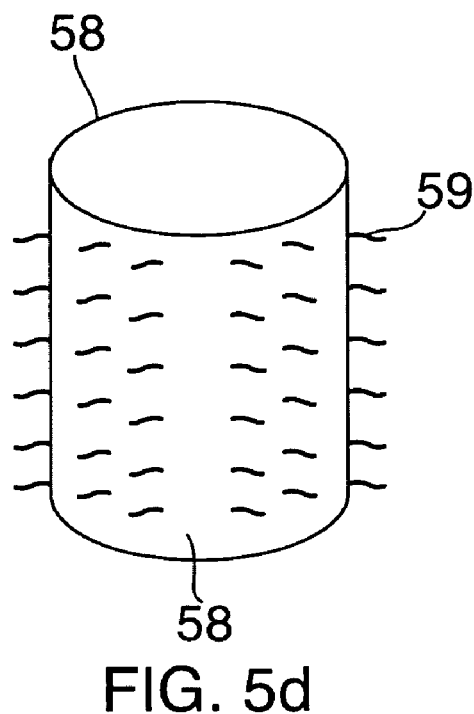

FIGS. 5c and 5d show a self-expanding sealing stent (such as that used in FIG. 4c) in accordance with another preferred embodiment of the present invention. One way to implement the self-expanding sealing stent is to build stent framework 56 from a shape memory material such as nitinol 56 and cover it with a layer of impermeable material 58. The self-expanding sealing stent is catheter-delivered to the cavity, whereupon the stent opens, its shape adjusting to the shape of the cavity and its impermeable covering 58 sealing the cavity, to prevent the paravalvular regurgitation. To anchor the self-expanding sealing stent in place, hooks 59 can be included on framework 56. Hooks 59 are attached to framework 56 and extend through sealing material 58 and into the wall of the aortic annulus. The hooks are self-extending. One way to implement them is to make them from a shape memory material such as nitinol.

Figure 6A:
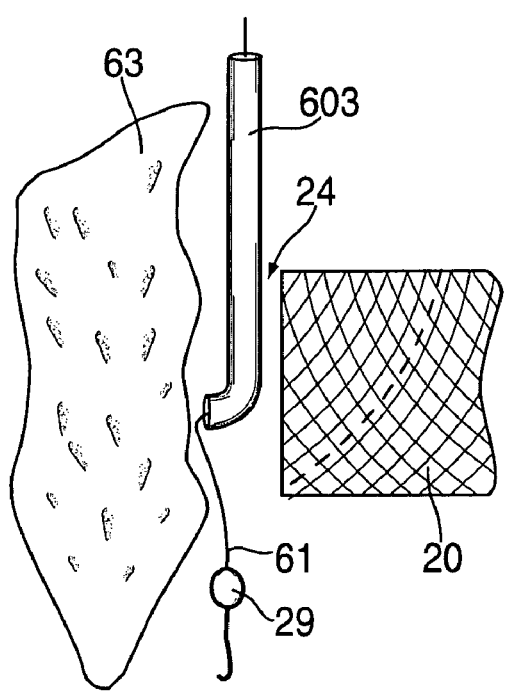
FIGS. 6a to 6d illustrate blocking a paravalvular leak with a sealing device, in accordance with another preferred embodiment of the present invention, assisted by anchors, which attach the device to the aortic wall (or annulus).
Figure 6B:
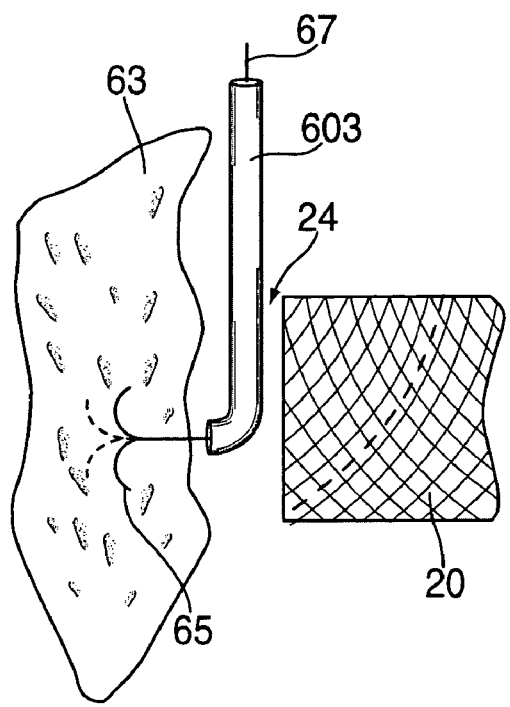
Figure 6C:
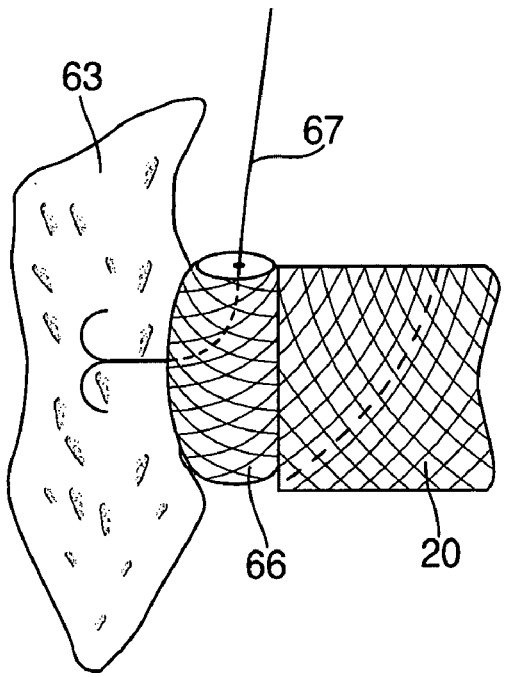
Figure 6D:
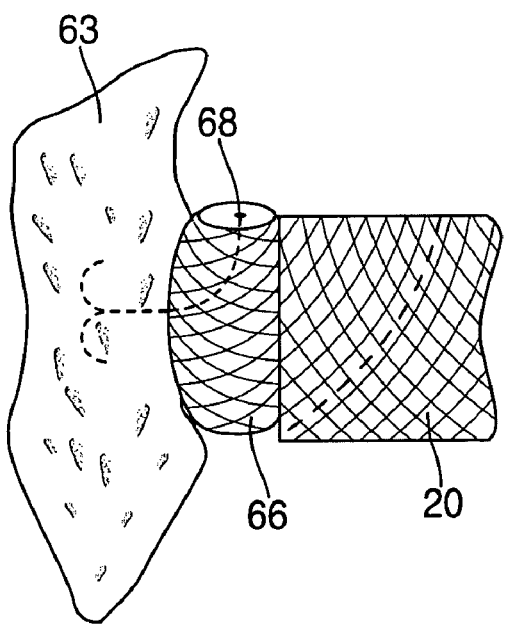

FIGS. 6a to 6d illustrate a technique for anchoring a sealing stent 66 (such as balloon-expandable sealing stent 47 or self-expanding sealing stent 48) into an open cavity 24, which is situated between aortic annulus 63 and prosthetic valve 20, and which creates paravalvular regurgitation. In FIG. 6a, a guidewire 61 is led through cavity 24 by balloon 29 (this can be done with a device such as those disclosed in FIGS. 1 to 3). Guiding catheter 603 is fed over the guidewire, and the guidewire is removed. In FIG. 6b an additional wire, anchoring wire 67, which terminates in anchoring apparatus 65, is inserted through catheter 63 to the anchoring location in cavity 24. Anchor 65 is a hook with one or more hook heads that can be compressed for delivery and will spring back to their original position when the delivery compression is removed (in other words, when the device emerges from the delivery catheter). Anchor 65 could be composed of flexible metal or a shape memory compound. Anchor 65 penetrates the aortic annulus at an approximately perpendicular angle due to the angled tip of guiding catheter 603. FIG. 6c shows sealing stent 66 inserted via anchoring wire 67 and expanded to seal the cavity by one of the methods described in FIG. 4 or 5. In the case shown in FIG. 6c, a self expandable sealing stent as described in FIG. 4 is shown. This method enables improved anchoring forces in comparison to friction alone, which is the sole anchoring for the embodiments shown FIGS. 4 and 5. FIG. 6d shows the final step of the procedure, where the wire is detached from the anchor at detaching point 68.

Figure 7:
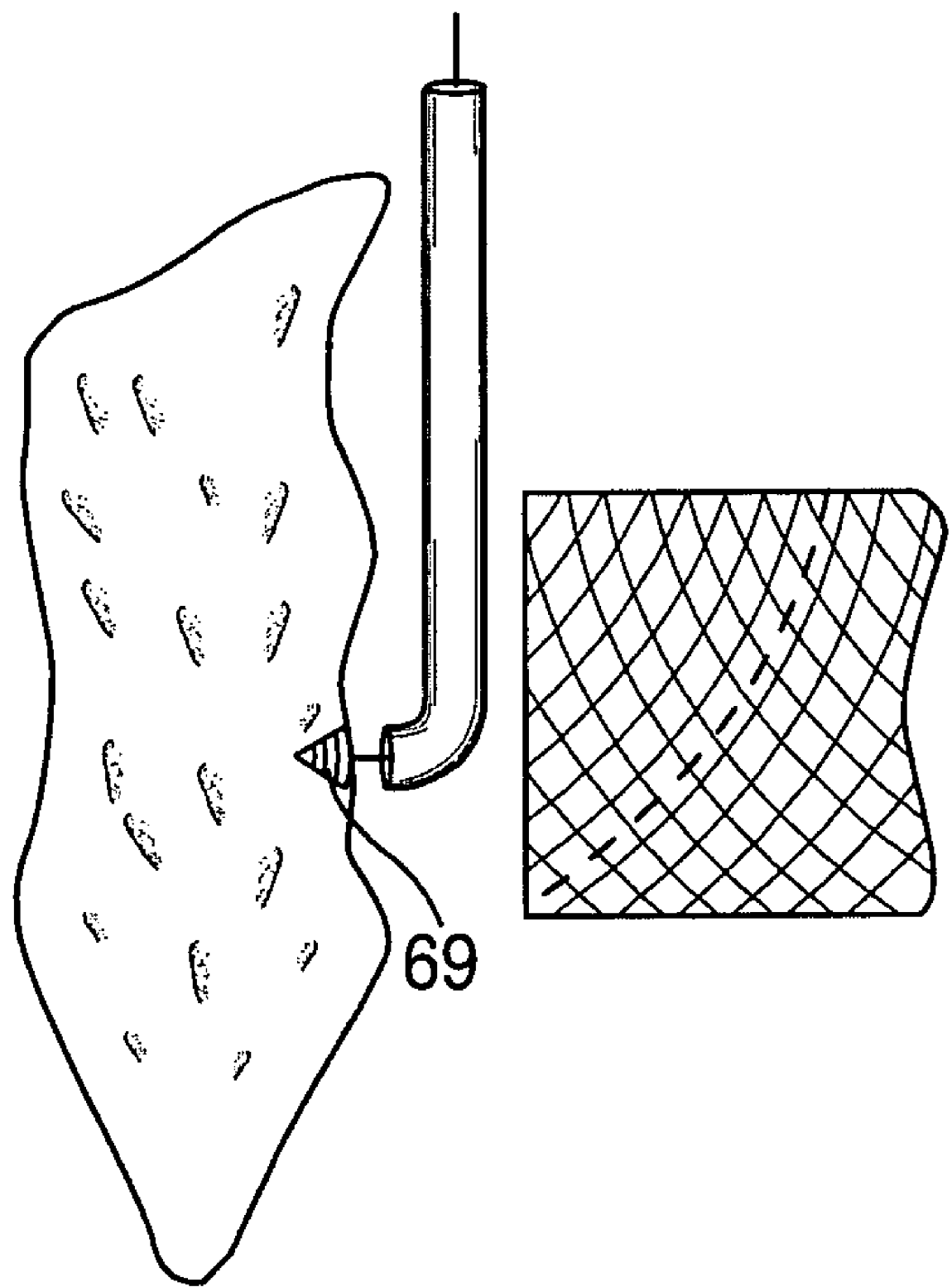
FIG. 7 illustrates an anchoring apparatus, in accordance with another preferred embodiment of the present invention, for achieving sealing as shown in FIG. 6, in this case by use of a screw, which is embedded into to the aortic wall (or annulus).

FIG. 7 depicts an apparatus that is similar to that illustrated in FIG. 6, only here anchor 65 is implemented as a screw tip 69. The anchoring is accomplished by rotating anchoring wire 67, thereby threading tip 69 into aortic annulus 22.

Figure 8A:
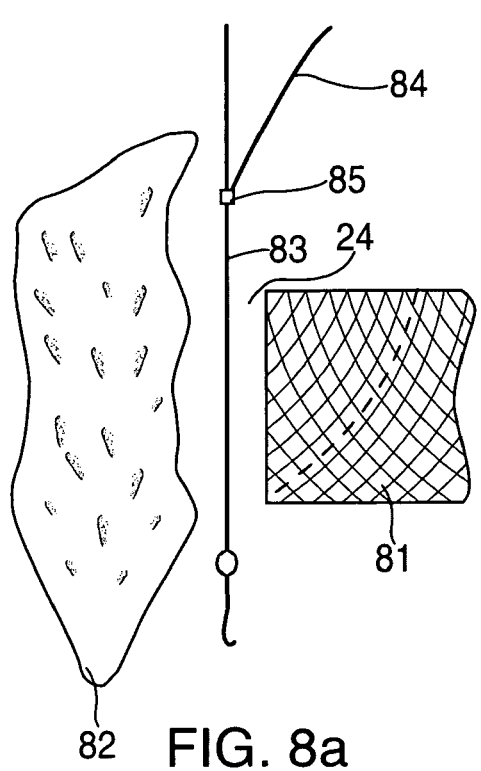
FIGS. 8a to 8d depict a leak repair done, in accordance with another preferred embodiment of the present invention, using a two-component biological glue.
Figure 8B:
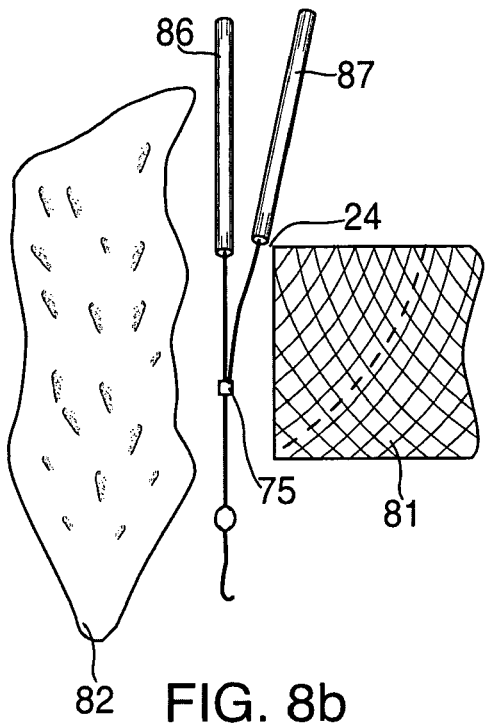

FIGS. 8a to 8d demonstrate an apparatus for repairing a paravalvular leak by means of biological bi-component adhesive material (such as an epoxy resin), the components of which are in liquid form and turn to solid when mixed, in accordance with another preferred embodiment of the present invention. The leak is caused by an open cavity between valve 20 and annulus 22. A leak detector, such as those shown in FIGS. 1 to 3, is used to run guidewire 83 through cavity 24. A second guidewire 84 with a slide element 85 is slid over the first guide wire 83. Slide element 85 enables second guidewire 84 to slide over first guidewire 28 and can be a ring at the end of second wire 84. In FIG. 8b, when slide element 85 and first guidewire 83 reach a point approximately midway through cavity 24, catheters 86 and 87 are slid over guidewires 28 and 84, respectively, until the catheters meet at meeting point 75.

Figure 8C:
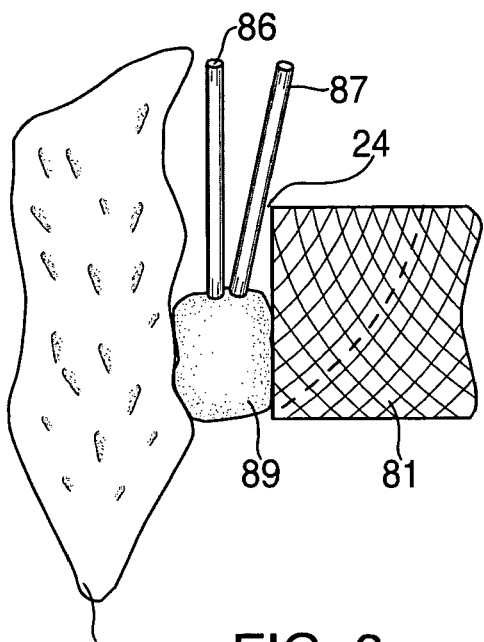
Figure 8D:
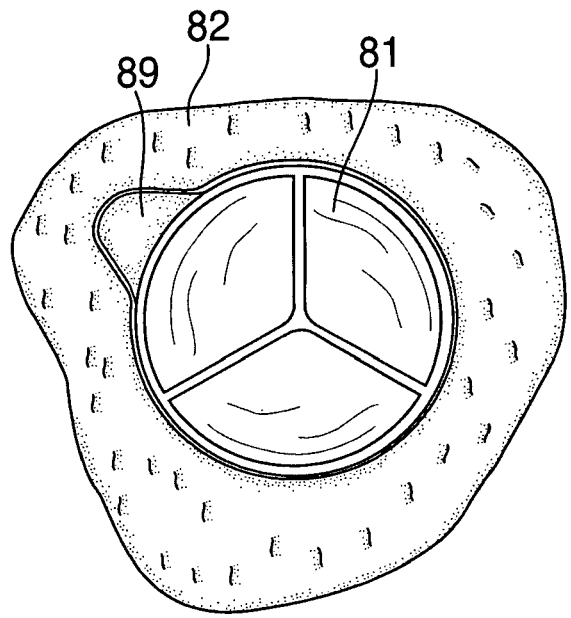

In FIG. 8c one of the components of a biological bi-component adhesive material is injected via catheter 86, and the other component is injected via catheter 87. The liquid adhesive components meet at the catheter outlets at meeting point 75, mixing to create the adhesive blocking element 89, which repairs the paravalvular leak by closing cavity 24. FIG. 8d depicts a top view of the final result of the repaired cavity showing that adhesive blocking element has been formed to seal cavity 24 between valve 20 and annulus 22.

Figure 9:
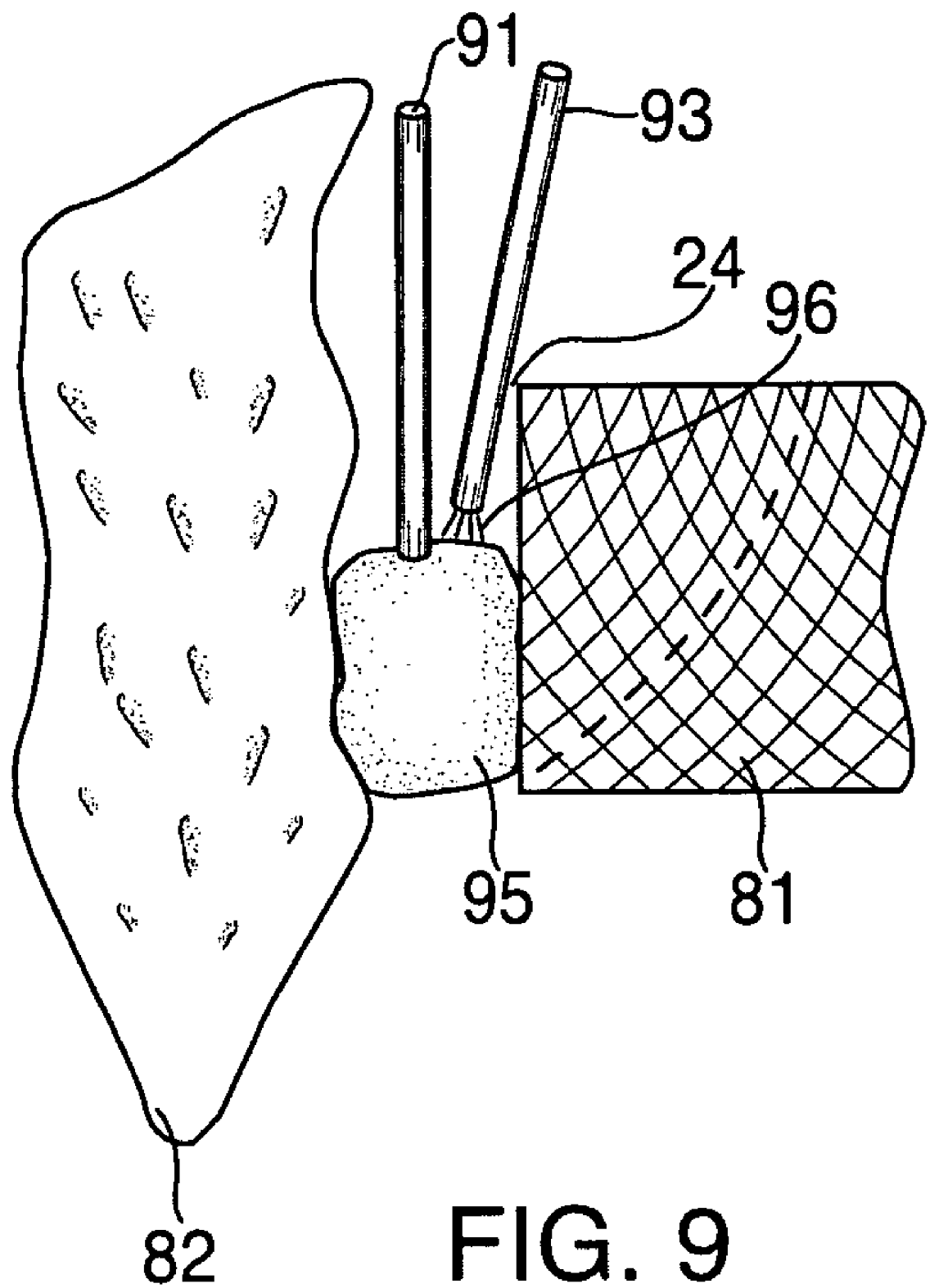
FIG. 9 depicts a leak repair done, in accordance with another preferred embodiment of the present invention, using an ultra-violet light cured biological glue.

FIG. 9 illustrates another apparatus for blocking a leak by means of biological adhesive in accordance with another preferred embodiment of the present invention. Again, two guidewires meet at meeting point 75, and catheters, in this case 91 and 93, are fed over the guidewires to meeting point 75. However, in this case the blocking adhesive material comprises one liquid component that is solidified by the presence of ultra-violet light or another radiation cure. The liquid adhesive material is inserted into cavity 24 at catheter meeting point 75 via catheter 91. Active wave 96 shining through light probe catheter 93 hardens the material, creating sealing block 95, which closes the leak caused by cavity 24.

FIGS. 10a to 10e illustrate another apparatus for repairing a paravalvular leak using a bi-component adhesive material in accordance with another preferred embodiment of the present invention. FIG. 10a shows a multiple-lumen catheter 100 that can be slid over guidewire 99 to the desired location, inside cavity 24 between aorta 82 and prosthetic valve 81. FIG. 10b is a cross-section of the catheter 100's multiple-lumen shaft. Lumens 102 and 103 provide means of approach for the separate components of the adhesive. Lumen 104 provides means for catheter to be fed over guidewire 28. FIG. 10c shows a bi-component adhesive infusion chamber 100 in the form of a double syringe connected to the end of catheter 100 that is proximal to the medical operator. FIG. 10d illustrates a mixing element 105 located at the distal end of catheter 100 (its location can be seen in FIG. 10a). Mixing element 105 serves to mix the two adhesive components as they emerge from distal end of catheter 100 after being forced out of chamber 101, thereby ensuring that they will solidify and cure inside cavity 24. FIG. 10e shows the adhesive components after they have been infused by chamber 101 via multiple-lumen catheter 100 and mixing element 105 into cavity 24 to form a plug. The cured adhesive fills the cavity and blocks the leak. Also shown in FIG. 10e is an optional flexible mesh bag 106, which receives and holds the adhesive mix. The bag prevents possible migration of adhesive material during insertion and prevents the adhesive from passing through stent struts 108 in cases where such valve designs are present.

FIGS. 11a to 11f illustrate an apparatus for repairing a paravalvular leak in accordance with another preferred embodiment of the present invention. Two self-expanding sealing stents 110 are connected by suture 112 and pushed into insertion catheter 111 (FIG. 11b). At this stage, insertion into the catheter has reduced the stents' diameter, enabling them to enter a cavity 24 between a prosthetic valve and surrounding blood vessel. FIGS. 11c and 11d depict an implanted valve 115 where two large calcifications 116 create cavity 117, which causes regurgitation and must be repaired. (The calcification is just one example of a condition that creates a cavity that must be repaired. The cavity could equally have been caused by other factors, the cause is not determinant for the embodiment.) FIG. 11e depicts insertion catheter 111 inserted over guidewire 28 to a point where the distal (delivery) end of the catheter has passed through the bottom of cavity 117. A first sealing stent 110 is deployed below the bottom of cavity 117. Catheter 111 is withdrawn and suture 112 is partially retracted, pulling the first sealing stent 110 into the bottom of the cavity, where it lodges. With reference to FIG. 11f, insertion catheter 111 is withdrawn until its distal end is near the top of cavity 24, whereupon a second sealing stent 110 is deployed. Suture 112 is further retracted, pulling the second stent into the top of the cavity, where it lodges. The final step of the procedure is to disconnect the proximal part of the suture at point 119.

Figure 12:
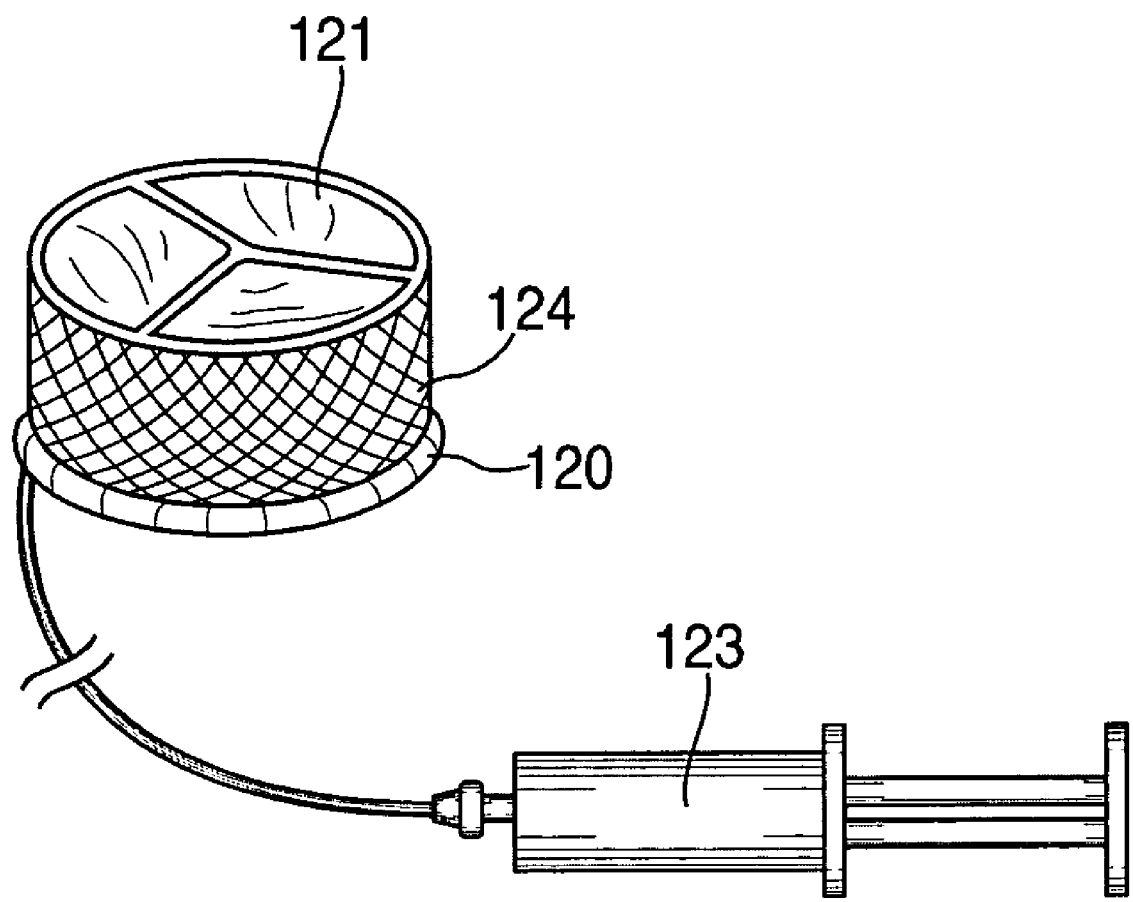
FIG. 12 depicts a valve, in accordance with another preferred embodiment of the present invention, with a built-in inflatable portion allowing to fill gaps between the valve stent and the aortic wall in order to prevent paravalvular leaks.

FIG. 12 depicts a valve adapted to seal paravalvular leaks in accordance with a preferred embodiment of the present invention. Valve 121 is held in holder stent 124 with sealing element 120 attached circumferentially around stent 124's outer surface. When valve 121 is implanted, sealing element 120 is expanded to seal any peripheral paravalvular leaks. Several means can be used to implement expansion of sealing element 120. In the implementation shown in FIG. 12, sealing element 120 is inflated by operator application of syringe 123, and it constitutes a balloon-like portion, made of a pliant physiologically acceptable polymeric material such as polyurethane. The inflation media can be saline solution, the patient's blood, or another physiologically acceptable fluid.

Alternatively, the sealing portion can be made of a material that, on contact with a fluid, soaks up the fluid and swells up. Once inserted into the body, the sealing portion comes into contact with the blood, causing it to swell and seal the cavity.

Figure 13A:
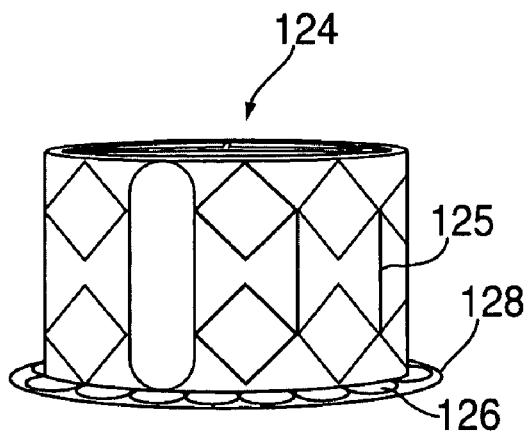
FIGS. 13a to 13d illustrate a valve, in accordance with another preferred embodiment of the present invention, having a flexible and self-expanding portion for blocking possible leaks around the stent.
Figure 13B:
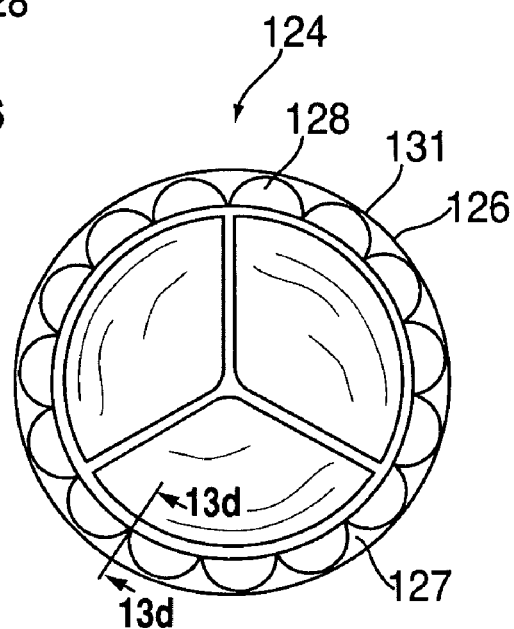

FIGS. 13a to 13d depict a valve adapted to seal paravalvular leaks in accordance with another preferred embodiment of the present invention. FIG. 13a depicts an implantable valve 124. Stent 125 has a sealing component 126 connected to its inlet. Sealing component 126 is comprised of a plurality of flaps 127 and expands to a larger diameter than the principal diameter of the stent 125, creating an extra sealing line to prevent paravalvular leaks. FIG. 13b depicts a top view of valve 124. Sealing component 126 comprises a plurality of flaps 127 that, independent of one another, are connected to the valve stent 125. Each flap 127 is made of spring wire 131, which, after the valve is deployed, causes flap 127 to extend out. Flaps 127 are covered with impermeable sealing material 128. Flaps 127 are arranged such that they are substantially perpendicular to the longitudinal axis of stent 124 and overlap one another, ensuring a full seal.

Figure 13C:
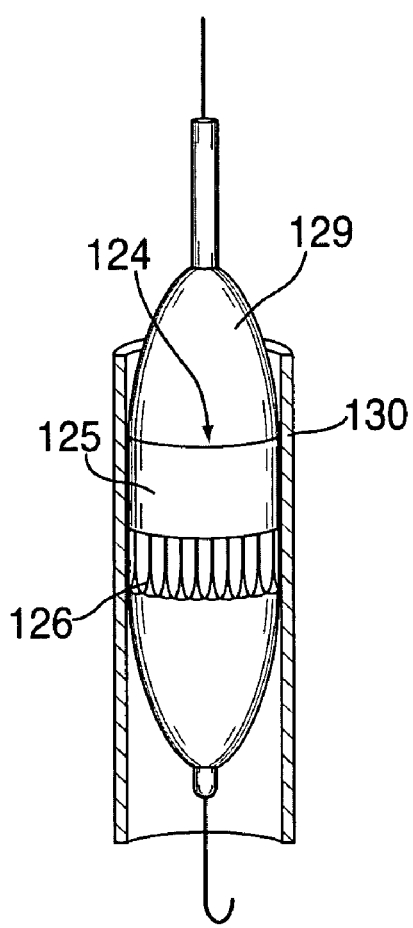

FIG. 13c shows stent-mounted valve 124 in its crimped configuration. Introducing sheath tube 130 holds stent 125 and sealing component 126 crimped on balloon 129. After deployment, flaps 127 of sealing component 126 open to their final diameter.

Figure 13D:
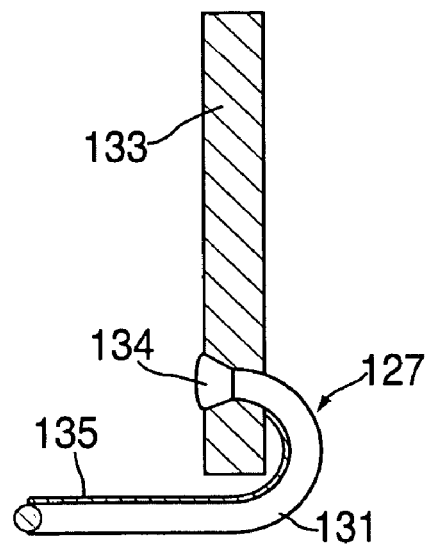

FIG. 13d shows a cross-section of a self-expanding sealing flap 127. Stent strut 133 is attached to spring wire ring 131 by mechanical attachment means 134, which can be a rivet, a screw, etc. Spring wire ring 131 can be folded into introducing sheath tube 130 shown in FIG. 13c and, when released from tube 130, springs back to its shape as shown in FIG. 13d.

Figure 14:
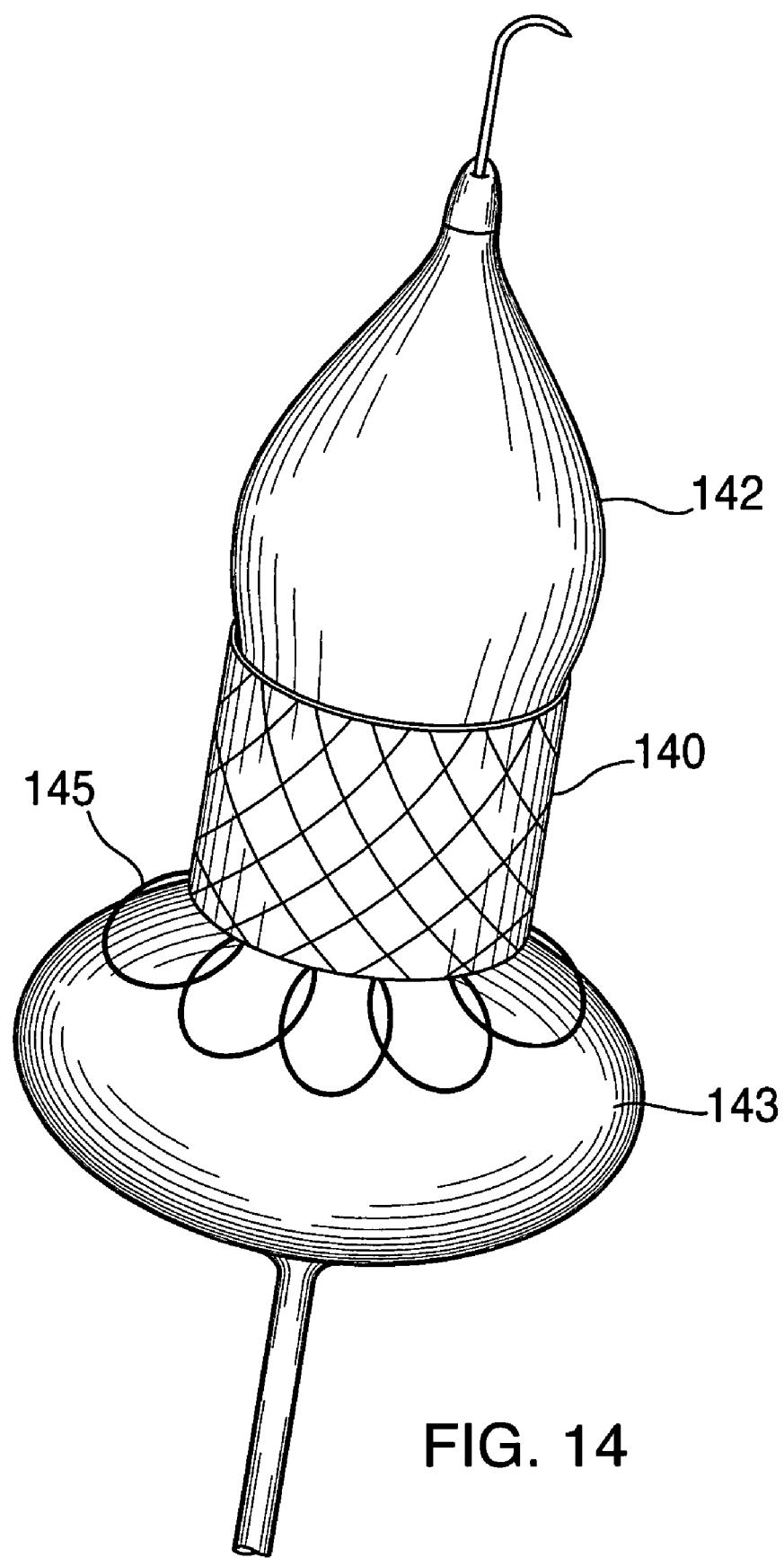
FIG. 14 illustrates a valve, in accordance with another preferred embodiment of the present invention, having a flexible and self-expanding portion for blocking possible leaks around the stent.

FIG. 14 illustrates a valve adapted to seal paravalvular leaks in accordance with another preferred embodiment of the present invention. This design includes balloon-inflatable stent 140 (containing a prosthetic valve) and balloon-inflated sealing ring 145, which is similar to sealing component 126 of FIG. 13, only here balloon-inflatable wire 145 is used instead of spring wire ring 131. Stent 140 is inflated using a double balloon. First balloon section 142 inflates stent 140 to the desired diameter, and then second balloon section 143 inflates sealing flaps 145 perpendicular to stent 140, creating a larger diameter and thus sealing any cavities around the stent.

Figure 15A:
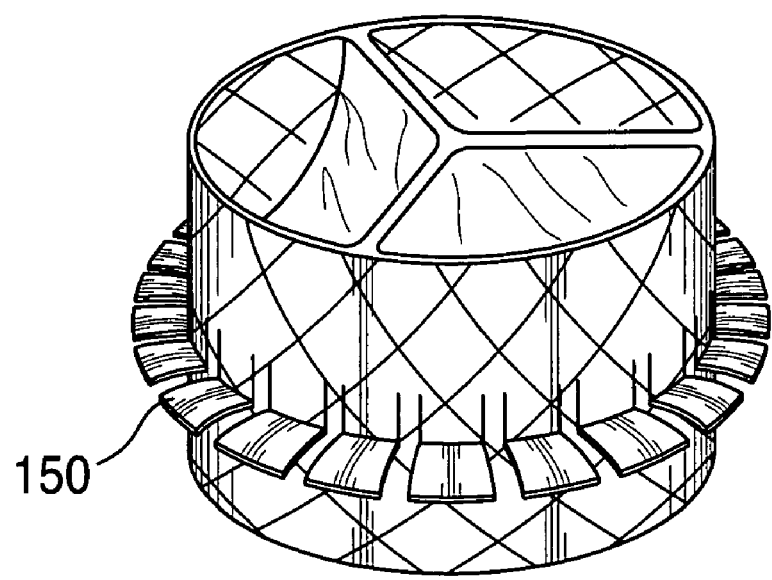
FIGS. 15a and 15b illustrate a valve, in accordance with another preferred embodiment of the present invention, having a plurality of flexible and expanding segments on its proximal side for blocking possible leaks around the stent.
Figure 15B:
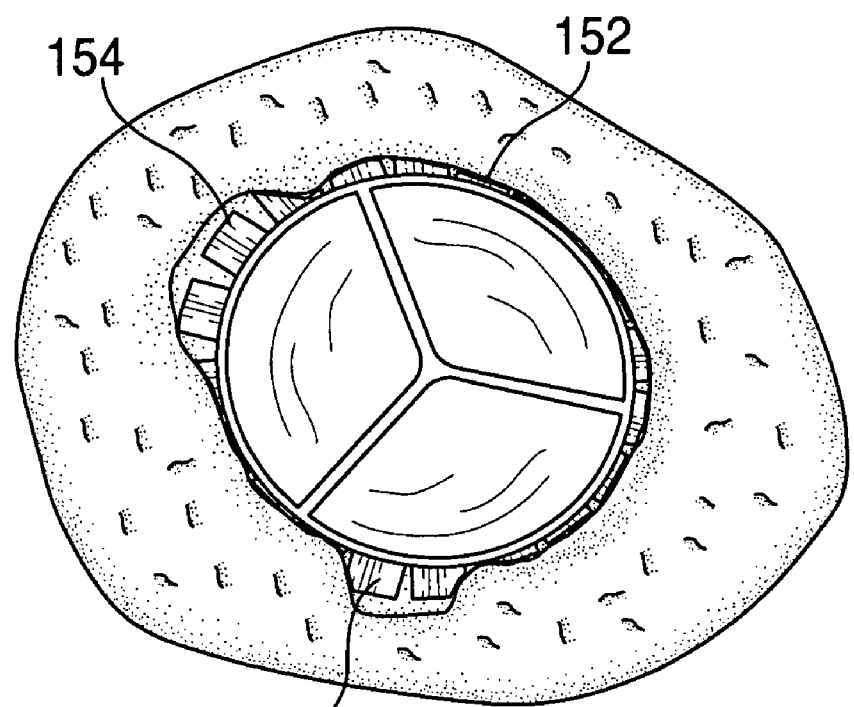

FIGS. 15a and 15b depict a valve adapted to seal paravalvular leaks in accordance with another preferred embodiment of the present invention. In this embodiment the sealing ring comprises flexible sealing elements 150. Each sealing element 150 is independently spring-actuated. When the valve is crimped, sealing elements 150 fold, enabling valve to be reduced to a small diameter for insertion. When valve is expanded to its final diameter, sealing elements 150 open to a larger diameter 154 to seal cavities around the valve, preventing paravalvular leaks. Since each sealing element 150 is independent, sealing elements adjacent to native valve tissue 152 remain closed. These closed elements provide a further benefit of adding compressive forces that improve the anchoring of the valve.

Figure 16A:
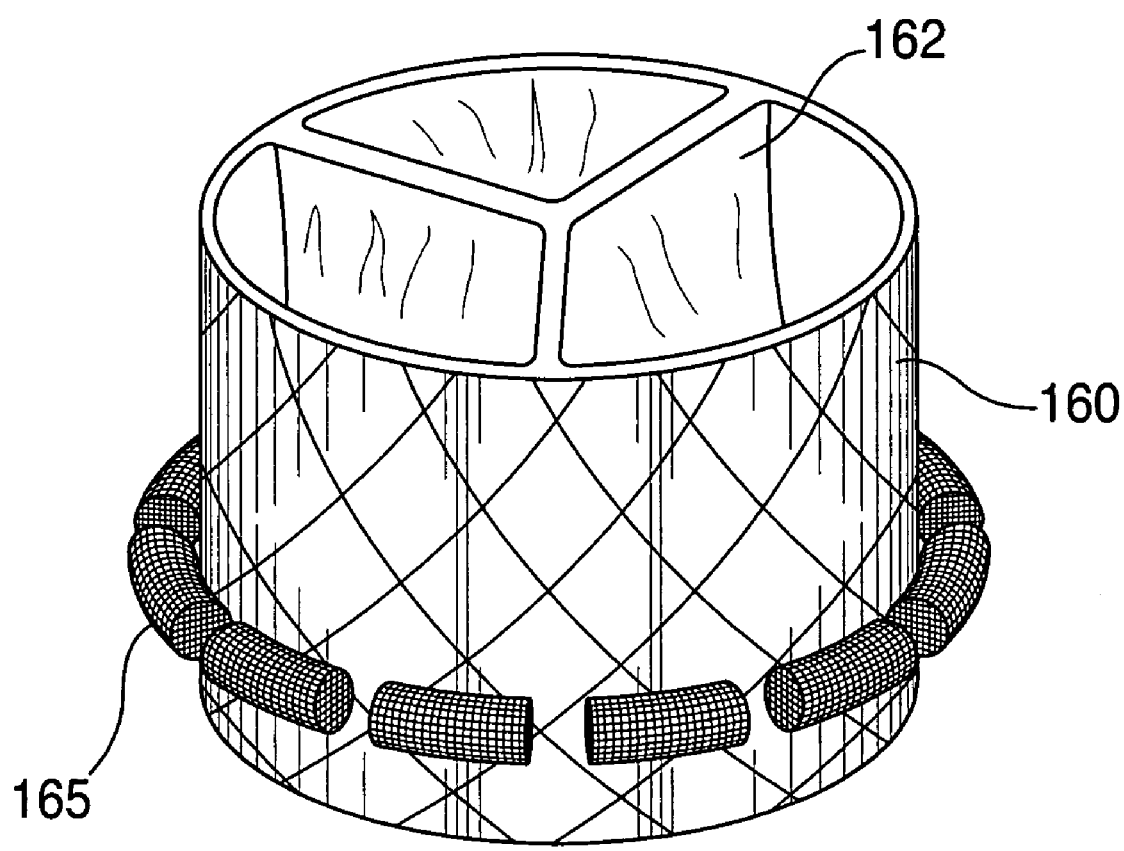
FIGS. 16a and 16b illustrate a valve device, in accordance with another preferred embodiment of the present invention, comprising an additional portion for blocking possible leaks around the stent.
Figure 16B:
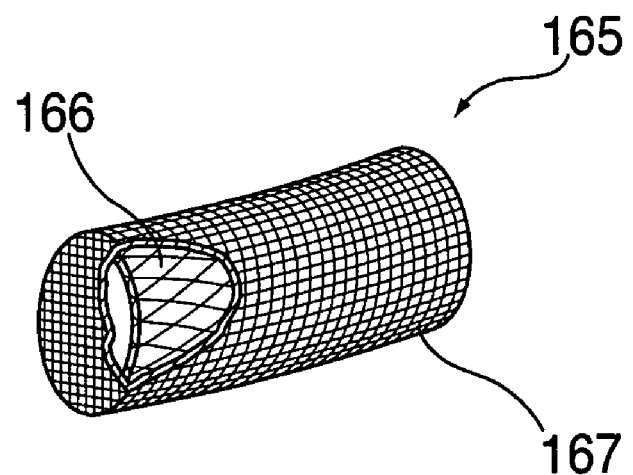

FIGS. 16a and 16b depict a valve adapted to seal paravalvular leaks in accordance with another preferred embodiment of the present invention. Here the sealing ring 165 comprises at least one of a plurality of flexible, self-expanding sealing elements 165 connected to the outer surface of stent 160. Similar to the embodiment shown in FIG. 15, when stent 160 is pressed against the native tissue, sealing element 165 will stay compressed against the wall. But where there is a gap between stent 160 and the surrounding tissue, sealing element 165 will expand and block any possible leak. With reference to FIG. 16b, sealing element 165 is made of self-expanding mesh 166 covered with PET (polyethylene terephthalate) mesh 167 or other impermeable material.

FIGS. 17a to 17e depict a valve adapted to seal paravalvular leaks in accordance with another preferred embodiment of the present invention, wherein the sealing component is built into a ring 172 of the stent struts. In the figure the ring of struts 172 is located at the stent's inlet; however, the ring of struts can equally be implemented at another point along the stent. The modified struts 173 comprising ring of struts 172 are designed so that they are geometrically constrained such that, upon expansion of the stent from crimped state (FIG. 17a) to expanded state (FIG. 17b), ring of struts 172 bend to a final diameter 169 substantially larger than the final diameter 168 of the rest of the expanded stent, thereby sealing paravalvular cavities and associate leaks.

FIGS. 17c and 17d show front and side views of the geometrical restriction in modified strut 173 that causes the displacement of point 175, creating enlarged diameter 169. FIG. 17c shows modified strut 173 before stent expansion and in line with the rest of the stent wall. FIG. 17d shows modified strut 173 after stent expansion, which has caused modified strut 173 to rise up and out, creating the sealing ring. FIG. 17e details the operation of the geometric restriction: when stent 170 is crimped, the strut legs are relatively close to each other 176, making strut height relatively large 177. After expansion, the strut legs are spaced further apart 176a, leading to displacement of point 175, and lessening of strut height 177a. The result of the movement of point 175 is shown in FIGS. 17c, 17d, and 17e. When the stent is crimped, as shown in FIG. 17c and the left side of FIG. 17e, point 175 is low. When the stent is expanded, as shown in the right side of FIG. 17e, point 175 moves up, pulling the stent to the shape shown in 17d.

Figure 18A:
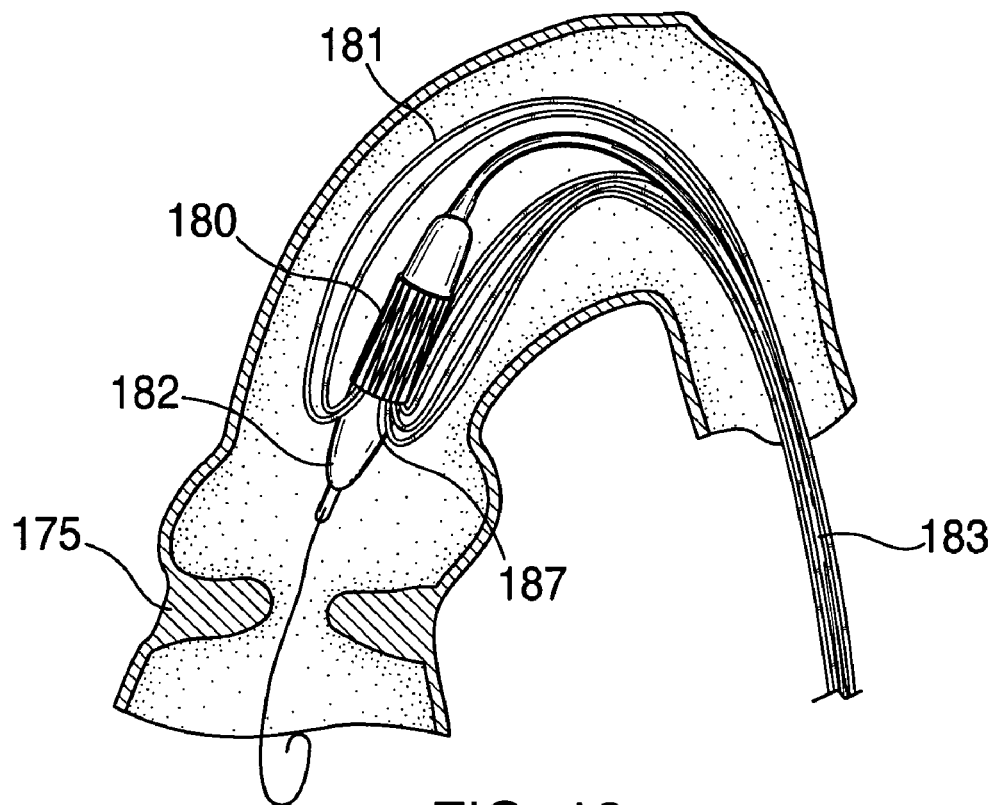
FIGS. 18a to 18e illustrate a valve, in accordance with another preferred embodiment of the present invention, constructed with additional sutures attached to the proximal side, allowing attachment of extra pieces of pericardium or artificial fabric for blocking paravalvular leaks.
Figure 18C:
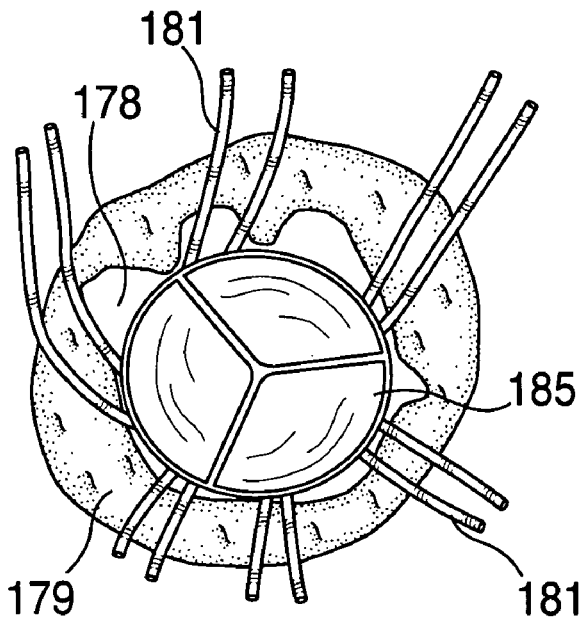
Figure 18B:
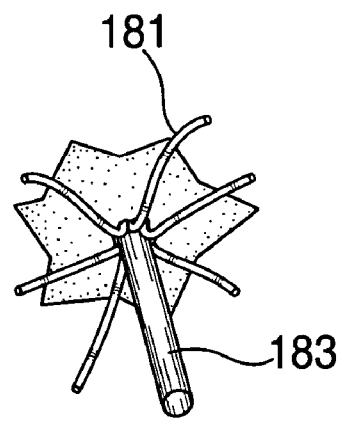

FIGS. 18a to 18e depict a valve adapted to include means for sealing paravalvular leaks in accordance with another preferred embodiment of the present invention. In FIG. 18a percutaneous valve 180 crimped on balloon 182 is shown being advanced toward the stenotic aortic valve 175. At least one of a plurality of sutures 181 are connected to valve 180 at inlet end 187. The sutures spread back along the balloon's shaft 183 and continue back along the deployment path and out of the patient's body as shown in FIG. 18b.

Figure 18D:
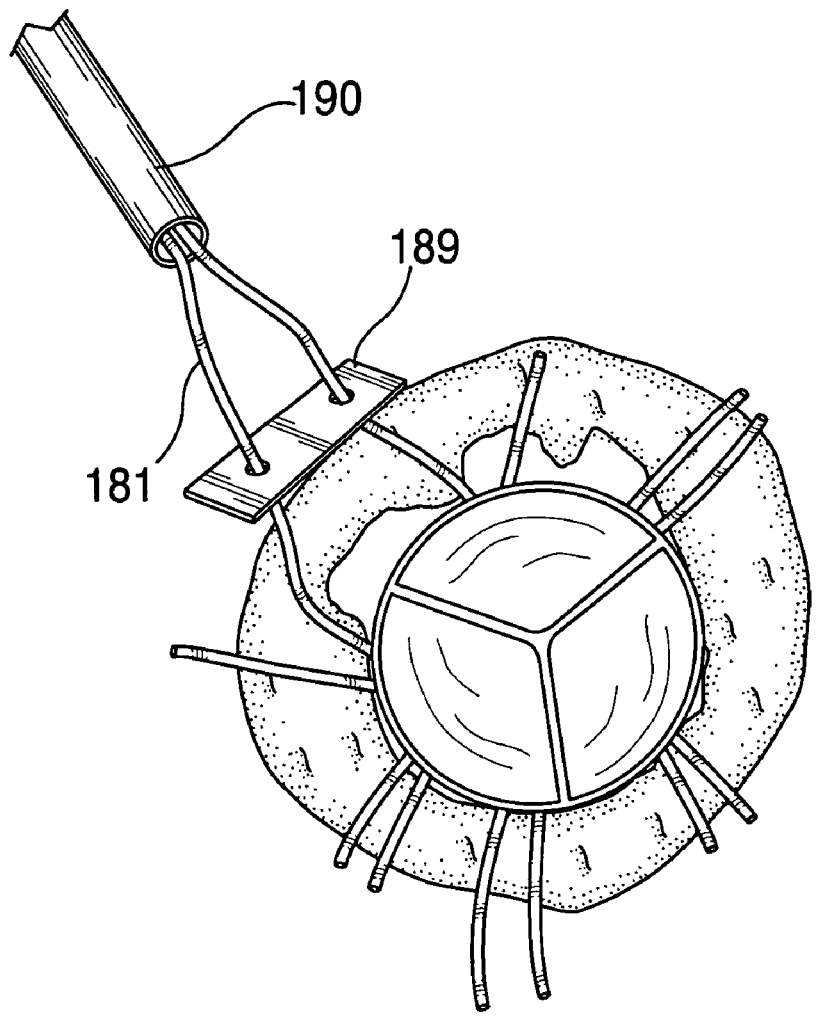
Figure 18E:
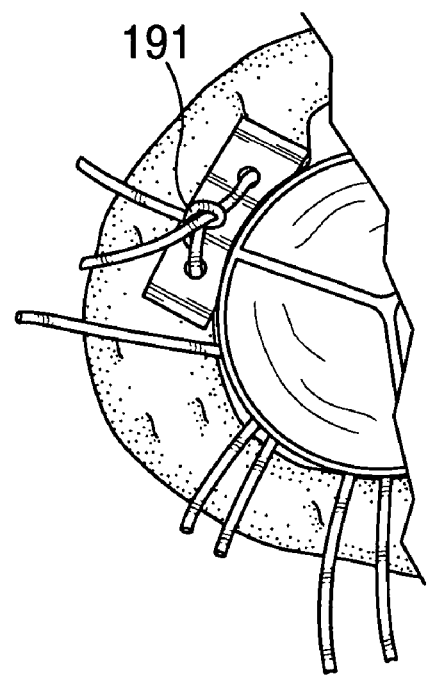

Inflating balloon 183, as shown in FIG. 18c, anchors valve 185 in annulus 179 with sutures 181 arranged around it. In cases where paravalvular cavities 178 are present, it is possible to repair them assisted by sutures 181. FIG. 18d shows a patch 189 made of pericardium (or other suitable patch material) inserted on sutures 181 and pushed to the leaking cavity by means of a pushing catheter 190. After the patch is in place, a knot or clip 191 is used to secure it, thereby repairing the leak (18e).

FIGS. 19a to 19d depict a valve adapted to include means for sealing paravalvular leaks in accordance with another preferred embodiment of the present invention. First elastic sealing stent 195 is inserted in the desired location. Then, valve 196 is inserted into sealing stent 195. FIG. 19a shows inserting catheter 191 with sealing stent 195 and valve 196 mounted on it. Sealing stent 195 and valve 196 can be either balloon inflated as shown in this figure, or self-expanding which would then require an introducing sheath.

FIG. 19b shows the two stents placed in the native aortic valve. Sealing stent 195 compensates for irregular shapes, while the stented valve 196, which is mounted inside sealing stent 195, can be absolutely round. Sealing stent 195 is able to avoid leaks caused by cavities or irregularities caused by pieces of calcification as described earlier in this patent. The sealing component of sealing stent 195 can be self-expandable hydrophilic sponge 197 (FIG. 19c) or other suitable material. Sealing stent 195 can include hooks 198 that open when the stent is inserted, improving the anchoring of the stent in the annulus as well as improving sealing around the stent by blocking blood (FIG. 19d).

The preceding specific embodiments are illustrative of the practice of the invention. It is to be understood, however, that other expedients known to those skilled in the art or disclosed herein, may be employed without departing from the spirit of the invention or the scope of the appended claims.

The invention claimed is:

1. A prosthetic valve with integrated sealing ring attached to the outside wall, the ring having a circumference greater than that of the valve and elastically conforming to seal cavities between the valve and the wall of the body vessel where the valve is implanted, the cavities producing paravalvular leaks during diastole wherein the ring comprises a plurality of spring-wire tabs mounted adjacent to one another around the circumference of the valve and covered with an impermeable membrane and wherein the tabs are folded against the body of the valve during catheter delivery and where, upon egress from the catheter, the tabs spring out to form the sealing ring.

2. A prosthetic valve with integrated sealing ring attached to the outside wall, the ring having a circumference greater than that of the valve and elastically conforming to seal cavities between the valve and the wall of the body vessel where the valve is implanted, the cavities producing paravalvular leaks during diastole wherein the ring comprises a plurality of impermeable tabs mounted adjacent to one another around the circumference of the valve, and further comprising a balloon under the tabs and wherein the tabs are folded down on the deflated balloon during catheter delivery and wherein, upon egress from the catheter, the balloon is inflated, hereby opening the tabs to form the sealing ring.

3. A prosthetic valve with integrated sealing ring attached to the outside wall, the ring having a circumference greater than that of the valve and elastically conforming to seal cavities between the valve and the wall of the body vessel where the valve is implanted, the cavities producing paravalvular leaks during diastole wherein the ring comprises a plurality of impermeable tabs mounted adjacent to one another around the circumference of the valve, each tab spring hinged to the valve and wherein the tabs are folded against the body of the valve during catheter delivery and wherein, upon egress from the catheter, the tabs spring out to form the sealing ring.

4. A prosthetic valve with integrated sealing ring attached to the outside wall, the ring having circumference greater than that of the valve and elastically conforming to seal cavities between the valve and the wall of the body vessel where the valve is implanted, the cavities producing paravalvular leaks during diastole wherein the ring comprises at least one of a plurality of flexible, self-expanding sealing elements comprised of self expanding mesh covered with an impermeable membrane.

5. A prosthetic valve with integrated sealing means, the sealing means comprising sutures attached around the perimeter of the valve and extending back out of the body and wherein patches can be pushed down the sutures and attached to the point where the suture is attached to the valve, thereby sealing any cavity existing between the valve and the wall of the body vessel where the valve is implanted, the cavities producing paravalvular leaks during diastole.

6. A catheter-delivered prosthetic valve with integrated sealing means, the sealing means comprising an elastic stent that is first deployed and inside which the valve is deployed, the elastic stent sealing any cavity existing between the valve and the wall of the body vessel where the valve is implanted, the cavities producing paravalvular leaks during diastole.

\* \* \* \* \*